United States Patent
Peters et al.

(10) Patent No.: US 12,166,448 B2
(45) Date of Patent: Dec. 10, 2024

(54) ROTARY MACHINE

(71) Applicant: Berlin Heart GmbH, Berlin (DE)

(72) Inventors: Oliver Peters, Berlin (DE); Valentin Bykov, Berlin (DE)

(73) Assignee: Berlin Heart GmbH, Berlin (DE)

(*) Notice: Subject to any disclaimer, the term of this patent is extended or adjusted under 35 U.S.C. 154(b) by 157 days.

(21) Appl. No.: 17/778,774

(22) PCT Filed: Nov. 23, 2020

(86) PCT No.: PCT/EP2020/083092
§ 371 (c)(1),
(2) Date: May 20, 2022

(87) PCT Pub. No.: WO2021/099641
PCT Pub. Date: May 27, 2021

(65) Prior Publication Data
US 2022/0416696 A1   Dec. 29, 2022

(30) Foreign Application Priority Data
Nov. 22, 2019 (EP) .................. 19 211 040

(51) Int. Cl.
*H02P 21/18* (2016.01)
*A61M 60/113* (2021.01)
(Continued)

(52) U.S. Cl.
CPC ............. *H02P 6/16* (2013.01); *A61M 60/113* (2021.01); *A61M 60/216* (2021.01);
(Continued)

(58) Field of Classification Search
CPC .................. H02P 6/16; H02K 29/12
See application file for complete search history.

(56) References Cited

U.S. PATENT DOCUMENTS

| 8,226,373 B2 | 7/2012 | Yaegashi |
| 9,746,345 B2* | 8/2017 | Baumann ............. G01D 5/2448 |
| 2019/0137536 A1* | 5/2019 | Yamamoto .............. G01P 1/026 |

FOREIGN PATENT DOCUMENTS

| DE | 695 03 613 T2 | 2/1999 |
| EP | 2 589 827 A1 | 8/2013 |
| WO | WO95/23297 | 8/1995 |

OTHER PUBLICATIONS

International Search Report with English Translation, dated Feb. 3, 2021, pp. 1-4, issued International Application No. PCT/EP2020/083092, European Patent Office, Rijswijk, The Netherlands.

* cited by examiner

*Primary Examiner* — Muhammad S Islam
(74) *Attorney, Agent, or Firm* — Crowell & Moring LLP

(57) ABSTRACT

The invention relates to a rotary machine comprising a stator and a rotatably mounted rotor, with one or more magnetic field sensors arranged stationary relative to the stator at a radial distance from a stationary axis, at least one measuring device which configured to detect magnetic field changes with the aid of the aforementioned magnetic field sensors, a rotor which is configured to generate one or more electrical signals in each case, said signals having signal components which correspond to the rotor rotation frequency and to the distance between magnetic field sensor and rotor in each case, wherein a demodulator unit carries out a demodulation of signals generated by or derived from the magnetic field sensors, such that a signal is generated which corresponds to the distance between the rotor and the magnetic field sensor.

16 Claims, 23 Drawing Sheets

(51) Int. Cl.
*A61M 60/216* (2021.01)
*A61M 60/462* (2021.01)
*A61M 60/816* (2021.01)
*A61M 60/82* (2021.01)
*A61M 60/825* (2021.01)
*H02P 6/16* (2016.01)

(52) U.S. Cl.
CPC ........ *A61M 60/462* (2021.01); *A61M 60/816* (2021.01); *A61M 60/82* (2021.01); *A61M 60/825* (2021.01)

a)

b)

c)

a)

b)

a)

b)

a)

b)

ROTARY MACHINE

CROSS-REFERENCE TO RELATED APPLICATIONS

This application is a 371 nationalization of international patent application PCT/EP2020/083092 filed Nov. 23, 2020, which claims priority under 35 USC § 119 to European patent application EP 19 211 040.1 filed Nov. 22, 2019. The entire contents of each of the above-identified applications are hereby incorporated by reference.

DETAILED DESCRIPTION

Figure 1:
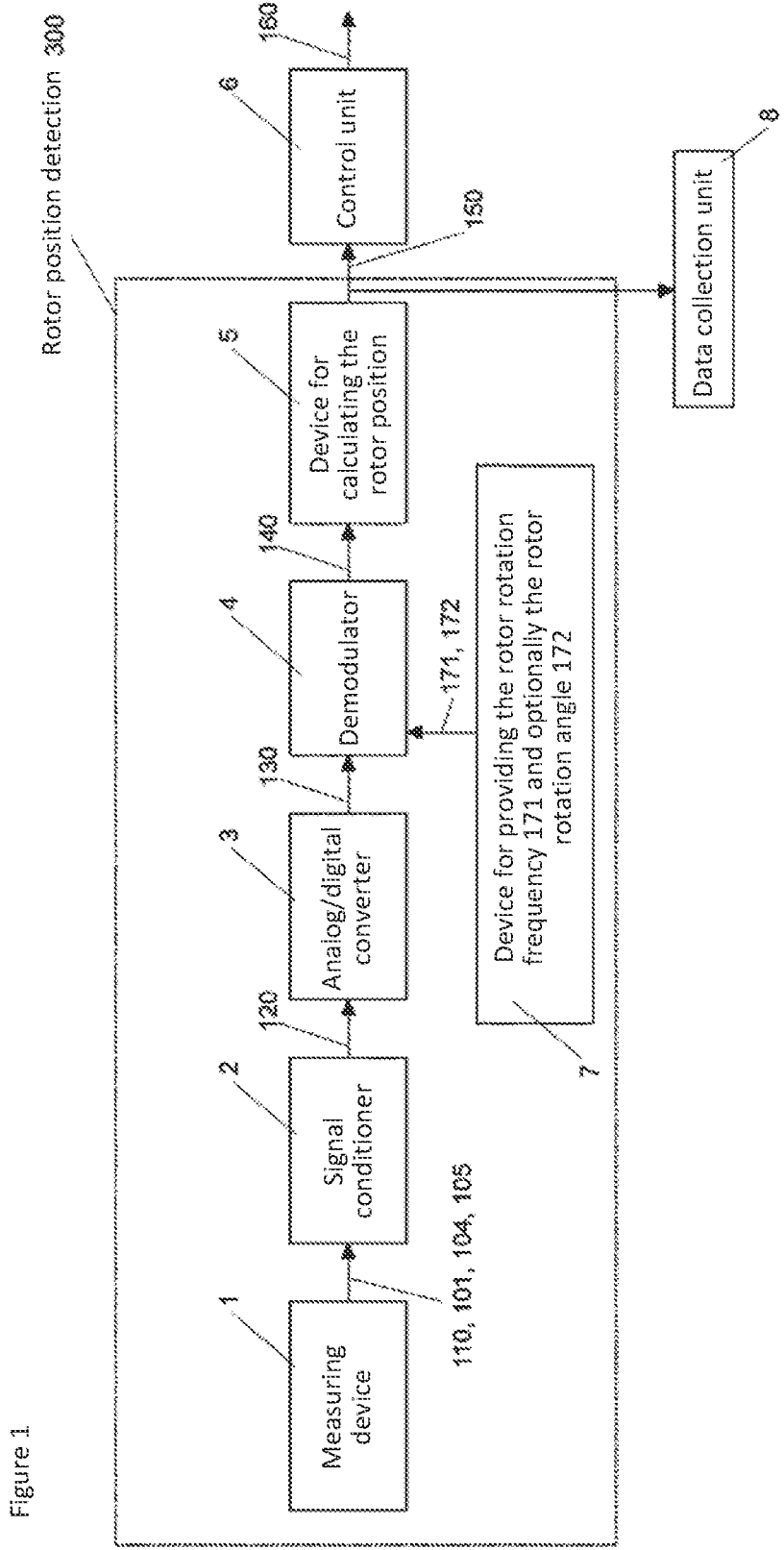
FIG. 1 illustrates a system overview.

The application relates to a rotary machine. Furthermore, said application relates to a method for operating the rotary machine and a system having a rotary machine.

Rotary machines are distinguished by at least one part arranged fixed relative to a coordinate system and generally referred to as the stator, and by at least one rotating part generally referred to as the rotor.

Examples of rotary machines include motors, compressors, turbines, among other things. Their fields of application are diverse. For example, motors or turbines can be used as drives, said drives in turn driving other machines that do work, such as compressors or pumps. Accordingly, rotary machines can themselves be used as a drive or as a driven machine. A combination of drive and working machine is also possible, for example, for motor compressors or pumps such as are used in heart support systems, for example, and in which a motor and a pump are integrated into one system. In this case, it is also possible for pump and motor functionality to be implemented with just one rotor.

Bearings, such as roller bearings, sliding bearings or magnetic bearings, are generally used as the intermediate element between the movable rotor and the fixedly arranged stator. Rotors can vibrate as a result of forces acting on the rotor, for example, those forces that occur during rotation due to imbalance forces or during use due to external forces. The vibrations in this case often contain both components corresponding to the rotor rotation frequency and, in addition to the actual rotation frequency, also contain harmonics of the rotation frequency. In addition, however, there is also the possibility that rotors vibrate at other frequencies that are not synchronous with the rotation frequency, for example, at resonance frequencies, the vibration frequency of which depends both on the rotor itself and on the bearing of the rotor. Whether and which of these resonance frequencies are excited depends, among other things, on the forces acting on the rotor.

In principle, said vibrations are transmitted to the stator via the bearings, so that said vibrations can also be detected as vibrations on the stator using vibration sensors. Limit values are generally specified for the permissible vibration values for continuous operation.

In general, one is interested in keeping the amplitude of the vibrations low both in the rotor and in the stator in order to counteract wear and functional impairments. Particularly in magnetic bearing machines, that is, machines in which the rotor is to be held in a defined target position relative to the stator by magnetic forces, there is often greater mobility of the rotor, said mobility being predetermined by a gap between the stationary stator and the rotatably mounted rotor. In order to detect the vibration level and possibly also to actively counteract it, the vibrations of the rotor are often measured continuously, in particular using distance sensors arranged fixed to the stator, said distance sensors measuring the relative distance between the sensor and the rotor and thus also between the stator and the rotor, so that conclusions can be drawn about the rotor vibrations from the time profile of said distance.

Although this method is widely used, a major disadvantage is that a complete measurement chain is required to detect the rotor position and, in addition, space must be provided for the sensors in the machine structure. Such a measurement chain can usually comprise components such as sensors, signal conditioners, amplifiers and also analog/digital converters. It can therefore be advantageous in certain embodiments to detect the rotor position without additional sensors, that is, to carry out the rotor position at least partially using means which are already present in the machine structure. In this case, one speaks of sensorless rotor position detection. Such systems are described, among other things, in patent specifications U.S. Pat. No. 9,506,475B2 and U.S. Pat. No. 8,226,373B2.

The object in the context of the rotary machine disclosed is to provide rotor position detection with which one or more components that are usually used in a measurement chain for rotor position detection can be omitted.

In addition to a stator, the rotary machine disclosed contains a rotatably mounted rotor, which is designed to move relative to the stator. An axis stationary relative to the stator is also defined for the rotary machine.

One or more magnetic field sensors are arranged stationary relative to the stator at a radial distance from said axis. Said magnetic field sensors in this case can explicitly have the special ability to carry out measurements for detecting the rotor position. However, said magnetic field sensors can also be part of other components, the main area of application of which is not the carrying out of measurements for the rotor position detection, but, for example, the drive of the rotor. Said magnetic field sensors can then be motor coils, for example, the main area of application being the generation of magnetic fields for the generation of forces to set the rotor in rotation. Each of the motor coils must be designed to generate a magnetic field suitable for driving the rotor. The axis stationary relative to the stator can, for example, run essentially parallel to the axis of rotation and can be used, for example, to define a target rotor position.

The rotary machine also contains at least one measuring device, which is designed to detect magnetic field changes with the aid of the aforementioned magnetic field sensors. The measuring device in this case also has the property of transforming the signals provided by the magnetic field sensors into the form of electrical voltages or electrical currents such that they are suitable for subsequent processing steps. For example, the measuring device can contain an impedance adjustment, a conversion of electrical voltages into electrical currents or electrical currents into electrical voltages, a reduction or increase in the amplitudes of electrical currents or voltages or also an analog-to-digital conversion.

Furthermore, the rotary machine contains a rotor, which is designed to generate one or more electrical signals in each case using one or more constant magnetic source voltages and using one or more of the magnetic field sensors, said signals having signal components corresponding to the rotor rotation frequency and to the distance between magnetic field sensor and rotor in each case. This means that components generating a magnetic field are arranged on the rotor, for example, permanent magnets or else electromagnets. When rotating, said magnets create a changing magnetic field. The aforementioned magnetic field sensors are arranged such that they are exposed to said changing magnetic field and generate signals corresponding to the strength of the magnetic field present at the respective time or its change in time and spatial orientation. This arrangement is typical for synchronous machines, but also for brushless DC motors or axial flux motors and generally for machines on the rotor of which magnets, for example, permanent magnets, are arranged, for example. In this case, the magnetic field sensors can be formed, for example, by motor coils, which are generally penetrated by the magnetic field of the magnets arranged on the rotor. In particular, there is a changing magnetic field when the rotor rotates, which leads to an induction of electrical voltage in the motor coils.

The arrangement consisting of the rotor equipped with magnets and the magnetic field sensors can also be interpreted as an amplitude modulator. The alternating magnetic field generated by the rotation of the rotor generates an electrical alternating voltage in the magnetic field sensors, which are designed as motor coils, for example, which, in the case of coils, is proportional to the change in the magnetic flux in the coils. On the one hand, the magnetic flux is dependent on the current position of the magnet in relation to the respective coil. On the other hand, however, the magnetic flux is also dependent on the configuration of the associated magnetic circuit, in particular on the materials used and the gaps existing in the magnetic circuit that contain materials that are not or only slightly magnetically conductive. In particular, the magnetic flux depends on the distance between the respective coil and the respective rotor magnet. Therefore, the magnetic flux is modulated by the rotor position relative to a coil and, accordingly, the electrical voltage in the respective coil is also modulated by the distance between the rotor and the coil. The resulting voltage signal therefore has the characteristics of an amplitude-modulated signal that is characterized by a carrier oscillation and a modulation signal that modulates the carrier oscillation.

In this case, the frequency of the carrier oscillation, the carrier oscillation frequency, is the frequency that results from the product of the rotor rotation frequency and the number of pole pairs of the rotor and the modulation signal is the respective distance between the coil and rotor. The carrier oscillation frequency is thus in a range that overlaps with the speed range of the motor or is closely adjacent to the speed range of the motor. The number of pole pairs of the rotor refers to the magnetic poles of the rotor, which are arranged in the vicinity of the respective magnetic field sensor and the magnetic field of which is designed to induce a voltage in the magnetic field sensors during rotation. The number of pole pairs is calculated from the number of said magnetic poles divided by two.

The rotor having the arrangement described is designed to be able to generate a distance-modulated signal using its magnets and the distance from the magnetic field sensor. This is of particular interest for motors in which magnets are already placed on the rotor, such as synchronous motors or brushless DC motors or axial flux motors.

The rotary machine further contains a demodulator unit, which is designed to carry out a demodulation on signals generated by the magnetic field sensors or derived therefrom, said signals having signal components corresponding to the rotor rotation frequency and the respective distance between the magnetic field sensor and the rotor, so that a signal corresponding to the distance between the rotor and the magnetic field sensor assigned to the respective signal is generated.

The demodulator unit is a component that carries out amplitude demodulation, for example. In general, the amplitude demodulation of a signal comprises the conversion of a signal frequency band, which is defined around a carrier oscillation frequency, into the range around the frequency 0 Hz. The practical implementation can take place, for example, using a known envelope demodulator or else by multiplication with a sinusoidal signal having the frequency of the carrier oscillation and subsequent low-pass filtering. In addition, further demodulation methods are known, for example, in which a periodic signal is multiplied instead of a sinusoidal signal, with the periodic frequency or a harmonic corresponding to the carrier oscillation frequency. The multiplication described can be carried out, for example, using an electronic mixer circuit. In addition, a frequency band can be converted with the aid of the Fourier transform. Such a method is preferably used in the digital domain, that is, time and amplitude discrete domain, since fast and efficient algorithms (Fast Fourier Transform—FFT) are available here for the calculation of the Fourier transformation.

There is also the option of at least one magnetic field sensor being designed as a coil in the rotary machine. If coils, which can then also be referred to as sensor coils, are used as magnetic field sensors, the voltage induced and measurable at the coil terminals is proportional to the change in the magnetic flux in the coil.

It has become clear from the previous statements and should be explicitly mentioned at this point that the rotary machine can be a motor.

It is also conceivable that at least one magnetic field sensor is designed as a motor coil and is designed to detect magnetic field changes and to generate a magnetic field suitable for driving the rotor. It is possible that, in order to actually move the rotor, a plurality of motor coils each have to generate a magnetic field suitable for driving the rotor. If current-carrying motor coils or bearing coils are used as magnetic field sensors, the voltage that can be measured at the coil terminals is the sum of the induction voltage due to the change in the magnetic flux in the coil, the self-induction voltage caused by the inductance of the coil and the resistive voltage drop at the resistance of the coil wire. A larger amplitude of the alternating magnetic flux thus leads to a proportionally larger alternating voltage component at the terminals of the coil. The magnetic field sensors can also be designed as differential Hall sensors. The signals generated by the Hall sensors are proportional to the magnetic flux.

In an electric motor, the coils generating a magnetic field suitable for driving the rotor, that is, the motor coils, can simultaneously be used to detect magnetic field changes. In this case, for example, components already present in the engine can take on this additional sensory task, so separate sensors are not required. Alternatively, sensors other than magnetic field sensors can nevertheless also be used, for example, differential Hall sensors or coils that are not motor coils primarily assigned to the drive.

The rotary machine can also be equipped with a device that makes the rotor rotation frequency available. There is the possibility of the rotor rotation frequency being made available by the motor controller, since this information may be available there anyway. In addition, however, it is also possible to measure the rotor rotation frequency, for example, by applying one or more markings to the rotor and detecting said markings by suitable sensors during operation. A possible example of a device for measuring the rotor rotation frequency, is, among other things, a narrow groove as a marker and a distance sensor aligned with the rotor, a so-called keyphasor, which is set so that when it passes the groove, also known as the keyphasor groove, it outputs a voltage signal that differs from the voltage signal it outputs in the phases of rotor revolution in which the keyphasor and keyphasor groove do not face each other.

Using a comparison device, the voltage signal generated by the keyphasor can be converted into a short voltage pulse per rotor revolution, which pulse can then be converted into a speed signal by a processing unit, for example, a counter assembly. A similar method is also possible on an optical basis, for example. The speed signal can ultimately be present in various forms, for example, as a voltage, current, as a numerical value, in the form of a pulse per revolution or as a periodic signal having a frequency that corresponds to the rotor rotation frequency. In principle, the rotor rotation frequency can also be carried out using a frequency analysis, for example, a Fourier transformation. A magnetic sensor signal is transformed into the frequency domain and the rotation frequency is detected by means of peak detection.

Optionally, the demodulator unit is designed to use the rotor rotation frequency for the demodulation. This is particularly the case when, in contrast to envelope demodulation, demodulation in the digital domain is carried out by means of a computer or microcontroller using the Fourier transformation, in particular the discrete Fourier transformation with its efficient implementation, the fast Fourier transformation or also, for example, using the Goertzei algorithm.

To do this, the signal to be demodulated is transformed into the frequency domain with the aid of Fourier transformation. With discrete Fourier transformation, the Fourier transformation of the signal is in a sampled state, that is, in the form of discrete values at frequency support points. For the demodulation, first all values at the frequency support points that do not belong to the carrier oscillation frequency, which corresponds to the rotor rotation frequency, and the amplitude-modulated signal are masked, that is, set to zero. The remaining, unmasked frequency support points are shifted towards the frequency of 0 Hz by the amount of the carrier oscillation frequency. All signal components that are shifted to the region around the frequency 0 Hz are added up and the resulting signal is transformed back into the time domain. The advantage of this approach lies in its simplicity. The disadvantage is that the phase position of the distance signal is lost and thus information that can be important for the generation of control signals in certain embodiments. It is still possible to determine at least the power of the rotor vibrations. Since the power can in principle also be determined in the frequency domain according to the Parseval theorem, the power of the rotor vibration can also be determined directly in the frequency domain. The power of the vibration can be used to evaluate the current vibration level and to generate control signals based thereon, such as an emergency shutdown.

The rotary machine can also be equipped with a device that provides the rotor rotation angle. The rotor rotation angle is an angle resulting from the rotation of the rotor, which angle is defined in a plane perpendicular to the axis of rotation of the rotor, the angle plane, and which results from the current position of a reference point on the rotor, a reference position of said reference point relative to the stator and the point of passage of the axis of rotation of the rotor through the angle plane, which is the vertex of the rotor rotation angle. The keyphasor groove, which is also used to determine the speed, can be used as a reference point, for example. The position of the keyphasor, for example, is suitable as a reference position relative to the stator. The current rotor rotation angle is finally determined with the aid of the current speed, with $$\text{rotor rotation angle} = (\text{rotor rotation frequency} * dt * 360 \mod 360),$$

where dt is the elapsed time since the reference point of the rotor last passed the reference position relative to the stator. Time can be measured using a clock or counter assembly, for example.

Using a known rotor rotation angle, the previously described method for demodulation in the frequency domain can be supplemented by a phase correction. In this case, phase correction means that an offset dependent on the rotor rotation angle is added to the phase angle of each Fourier coefficient, so that the phase position of the signal corresponds to the phase position of the rotor vibration signal during the inverse transformation into the time domain.

In addition, using the rotor rotation angle, it is possible to carry out the demodulation of the signal by multiplying it by a sinusoidal oscillation with the aid of an electronic circuit. For this purpose, an oscillator is used, for example, to generate a frequency which corresponds to the carrier oscillation frequency and which adjusts the phase position of the generated frequency, for example, using a phase-locked loop, so that it corresponds to the phase position of the carrier oscillation. The phase position in this case can be extracted directly from the phase position of the carrier oscillation or alternatively can also be calculated from the rotor rotation angle.

Optionally or additionally, the rotary machine contains a first processing unit, which is designed to superimpose and/or filter one or more electrical signals from the aforementioned magnetic field sensors into one or more signals such that the signal component in the resulting signal in each case, said signal component, which contains information on the distance between the rotor and the respective magnetic field sensor, is in each case amplified in relation to other signal components.

This first processing unit can be implemented as an analog circuit and can contain, for example, adder or subtractor circuits or also filter circuits, which can be implemented, for example, with operational amplifiers. In principle, however, said first processing unit can also be partially or completely digital, for example, as a digital computing unit based on one or more microcontrollers, processors, user-specific circuits or in field programmable gate arrays or alternatively with discrete components.

For signal superimposition of the signals measured by the magnetic field sensors possible in the first processing unit, there is the option, for example, of adding up a plurality of the measured signals in the correct phase such that signal components that do not contain any information about the position of the rotor are eliminated. This option can be used advantageously in certain embodiments if the rotary machine is an electric motor, for example, and drive-related magnetic field components make up a high proportion of the measured magnetic field power or signal components that are independent of the rotor axis position are superimposed on the rotor position signal.

If the signal filtering of the signals measured by the magnetic field sensors is possible in the first processing unit, there is the option, for example, of advantageously using frequency-selective filters, for example, low-pass filters, in certain embodiments, so that all signal components that lie outside of the frequency band that contains information about the rotor position are suppressed, that is, attenuated in the measured signals. Such signal components to be suppressed can, for example, be signal components originating from the motor controller. Motor control signals can be pulse width modulated, for example, with the switching frequency of the pulse width modulation being several thousand Hertz, for example. The switching frequency and its harmonics can be suppressed by low-pass filtering.

The rotary machine can also contain a second processing unit, which is connected downstream of the demodulator and which is designed to generate one or more rotor position signals from the demodulated signals. The demodulated signals contain a signal corresponding to the distance between the rotor and the respective magnetic field sensor. Since the change in magnetic flux is proportional to the alternating frequency of the flux, the amplitude of said distance signal corresponds not only to the distance between the magnetic field sensor and the rotor, but also to the frequency of the carrier oscillation, which in turn is related to the rotor rotation frequency. In order to eliminate this dependency from the signal, the distance signal is first scaled as a function of the speed and then, with the aid of the known position of the magnetic field sensors and the determined distance information between the magnetic field sensors and the rotor, the rotor position is determined relative to a coordinate system fixed to the stator. This is usually, but not necessarily, a Cartesian coordinate system. Rotor position signals are generated based on this coordinate system, said rotor position signals representing the coordinates of the rotor relative to this coordinate system for each measurement time. Preferably, these are coordinates that describe the rotor position perpendicular to the axis of rotation or also parallel to the axis of rotation.

The rotary machine can also preferably contain a control unit, which is designed to generate control signals from the rotor position signals. The control unit can, for example, be a monitoring unit which, for example, performs an emergency shutdown of the entire system if the rotor vibrations are too great, triggers a speed change, actuates control valves or causes alarm signals to be output, for example, optical or acoustic. In addition, the rotor position signals can be logged. Alternatively, the control unit can also be designed as a regulation device that generates control signals that exert one or more forces on the rotor via one or more actuators, which influence the rotor vibrations, in particular the position or the speed of the rotor relative to the stationary magnetic field sensors. The actuators can be, for example, a vibrating element that, for example, transmits vibrations to the stator, as a result of which, for example, a force can be transmitted to the rotor via the bearing, which can lead to attenuation of the rotor vibrations. A prerequisite for an attenuation effect is that the vibration of the vibrating element is generated in the correct phase. Other actuators for exerting a force on the rotor are, for example, electromagnets or piezo actuators.

For monitoring, later evaluation of the signals or possible troubleshooting, it makes sense to optionally equip or connect the rotary machine to a data collection unit, which is designed to store one or more determined position values of the rotor. For this purpose, the data collection unit can be fitted in or on the rotary machine. Alternatively, however, it can also be arranged spatially separately from the rotary machine, for example, on a remote server.

The application for the rotary machine also relates to a method using the arrangement described above. Essential key points of the method are that, in a first step, electrical signals are measured at the magnetic field sensors and, in a second step, said signals or signals derived therefrom are demodulated. The electrical signals can be currents or voltages that are generated by the magnetic field sensors. The demodulation can be carried out using various methods, for example, as envelope demodulation or also using the rotor rotation frequency in the time or frequency domain, optionally also using the rotor rotation angle.

An optional intermediate step can be provided before the demodulation, in which one or more electrical signals from the aforementioned magnetic field sensors are processed into one or more signals such that the signal component in the resulting signal, which contains information about the distance between the rotor and the respective magnetic field sensor, is in each case amplified in relation to other signal components. This task can be performed, for example, by using frequency-selective filters, such as low-pass filters, or by linearly combining one or more signals from the magnetic field sensors.

Furthermore, in a further method step, there is the possibility of a rotor position and/or a linear displacement speed and/or a linear acceleration of the rotor axis being determined from the demodulated signals. To determine the rotor position, the position of the rotor is preferably determined in the form of coordinates of a coordinate system, starting from the known positions of the magnetic field sensors and with the aid of the determined distances of the rotor from the magnetic field sensors.

In an optional method step, control signals can be generated from the rotor position signals. Said control signals can be used for monitoring, for example, in order to be able to bring about an emergency shutdown if the vibration values are too high, or to change certain operating parameters. For example, the control device can trigger a speed change, activate control valves or cause alarm signals to be output, for example, optically or acoustically. In addition, logging of the rotor position signals can be triggered.

Furthermore, the control signals can also be used to influence the position or the speed of the rotor relative to the stationary magnetic field sensors, for example, with the aid of electromagnetic actuators, piezo actuators or vibrating elements, and thus actively counteract vibrations. Actuators can be, for example, electromagnets in the form of motor coils or the electromagnets of an active magnetic bearing. The control signal can be generated, for example, with the aid of a regulator, which has a PID characteristic, for example, or can optionally be supplemented with further filter elements. The regulator can also, optionally, be designed as a multivariate regulator in a state space representation, in which the regulator parameters are determined using an optimization method, for example, an H∞ method. The influencing of position and speed is aimed at influencing the central position of the rotor and dampening the tendency of the rotor to vibrate.

If the magnetic field sensors are designed as motor coils having a center tap, the disclosed method is optionally designed to generate one or more control signals for the symmetrical or asymmetrical control of one or more motor coils and in this way to influence the position or the speed of the rotor relative to the stationary magnetic field sensors. With symmetrical activation, the control current is impressed in the motor coils of one phase such that the activation at the phase terminal and thus for the motor controller is not noticeable. For asymmetrical activation, for example, when only one motor coil of a phase branch is activated, the currents at the phase terminal caused by the activation do not cancel each other out.

In a further embodiment, a motor phase or part of a motor phase is bypassed with a regulated bypass, consisting of a switching element, for example, a transistor. The regulated bypass shunts some of the motor coil current past the motor coil, thereby weakening the force or torque produced by the stator. The regulated bypass has a control input that specifies the strength of the attenuation. The regulated bypass is an energetically passive system and thus enables the integration of power generation, for example, to dampen vibrations, in a motor without energy supply for the actuators.

Figure 22:
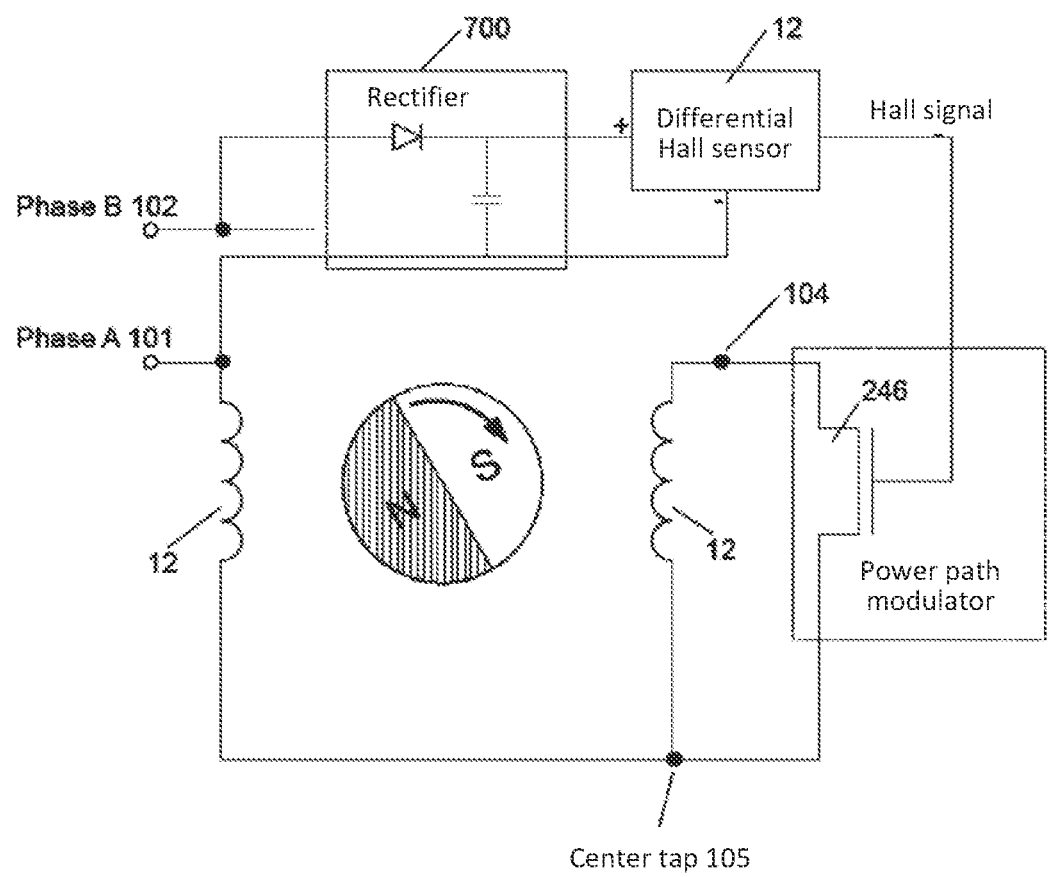
FIG. 22 illustrates an energetically passive implementation of the damping control loop with self-mixing.
Figure 23:
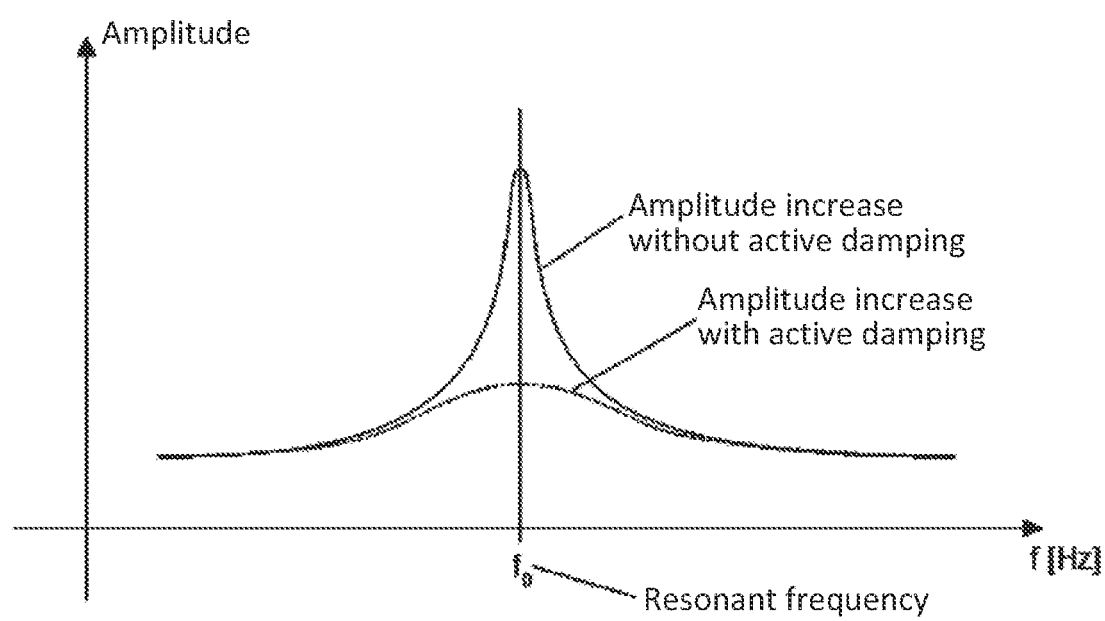
FIG. 23 illustrates an exemplary amplitude response of a dynamic system with and without active damping.

A particular advantage arises when combining a rotor position sensor element, which is demodulated with the rotation frequency, with an actuator element, which is modulated with the rotation frequency. Demodulation and modulation cancel each other out and can be omitted. This effect is referred to here as self-mixing. The sensor elements from FIGS. 1 to 15 are particularly suitable therefor. Sensor elements that impress an external signal are not suitable therefor. The omission of demodulator and modulator results in a very compact damping system which, in combination with the regulated bypass, can also be constructed in an energetically passive manner (FIG. 22). The price for compactness is that the position signal is not available and cannot be measured or monitored.

Optionally, the disclosed method is designed such that a force or a torque acting on the rotor is determined from the rotor position signals. The rotor position not only indicates the position relative to a coordinate system fixed to the stator, but also the position relative to a bearing that is used to support the rotor. For example, rolling, gliding or magnetic bearings can be used. Said bearings each have a known stiffness, so that a force can be determined directly via the stiffness proportionality factor, with which force the rotor is pressed into the bearing. In addition, it is possible to determine a torque relative to a rotor-fixed point using this acting force. When using actuators to regulate the rotor position, the force exerted by the actuators must be taken into account when determining the force or torque acting on the rotor.

Optionally, the disclosed method can be designed so that, using tables stored in the pump controller, or simple, multidimensional approximations with polynomials of the nth degree (preferably not higher than 4), flow parameters such as pressure distribution, pressure generation or the flow rate are inferred from the rotor position and the torque acting on the rotor. Among other things, this can also be done in combination with the speed and power consumption of the motor and an estimated viscosity. Furthermore, the movement of the rotor, in particular its movement frequencies, can be used to detect thrombi in the region of the pumps and to estimate the viscosity of the blood.

Furthermore, the force acting on the rotor or the torque acting on the rotor can be evaluated in order to infer system parameters such as aging, wear, corrosion or biological growth.

In addition, within the scope of the disclosed method, one or more determined rotor position values can optionally be stored in a data collection unit. Furthermore, it is also possible to store further secondary data in the data collection unit, such as the determined force, the torque and further estimated parameters related to aging, wear, corrosion or biological growth.

Embodiments are described below with reference to figures.

The basic system components of the rotor position detection 300, the control unit 6 and the data collection unit 8 are shown in FIG. 1.

The measuring device 1 is primarily designed, also in superimposition to motor signals, to detect one or more magnetic fields or changes in said magnetic fields, to convert them into electrical current or voltage signals and to bring said voltage signals into a form that said signals can be processed further. For this purpose, the measuring device 1 comprises magnetic field sensors 12 and, for example, electrical connectors and terminals and optionally measuring amplifiers, level converters or impedance converters. Electrical signals 101, 102, 103, 104, 105, 106, 107 or 110 are made available for the optional signal conditioner 2 at the output of the measuring device 1. The signal conditioner 2 performs signal preprocessing, in the course of which the signal component containing information on the rotor position or information on the distance between a magnetic field sensor and the rotor is amplified relative to other signal components. This can be done, for example, by frequency-selective filtering, in which only the relevant information is left in the signal, or by a linear combination of a plurality of measurement signals. The output signal 120 of the signal conditioner 2 is optionally converted to a digital signal using the analog/digital converter 3. In principle, it is possible for the analog/digital converter 3 to be integrated into the signal conditioner 2, so that further signal conditioning methods can optionally also be inserted after the analog/digital converter 3. The output signal 130 of the analog/digital converter 3 serves as an input signal for the demodulator 4, which is designed to carry out amplitude demodulation. The demodulation is analog or digital, depending on whether the optional analog/digital converter 3 is used. There is also the possibility of, with the aid of the device 7 for providing the rotor rotation frequency 171 and the optional rotor rotation angle 172, for the rotor rotation frequency 171 and/or the rotor rotation angle 172 to be used in the amplitude demodulation. At least one component, preferably a plurality of components, of the rotor position, in particular at least that component of the rotor position which can be regulated, is determined in the device 5 from the demodulated signals 140. The output signal 150 thereof is used in an optional control unit 6 to generate control signals 160. The measured and/or calculated signals and data can optionally be stored in a data collection unit 8.

Figure 2:
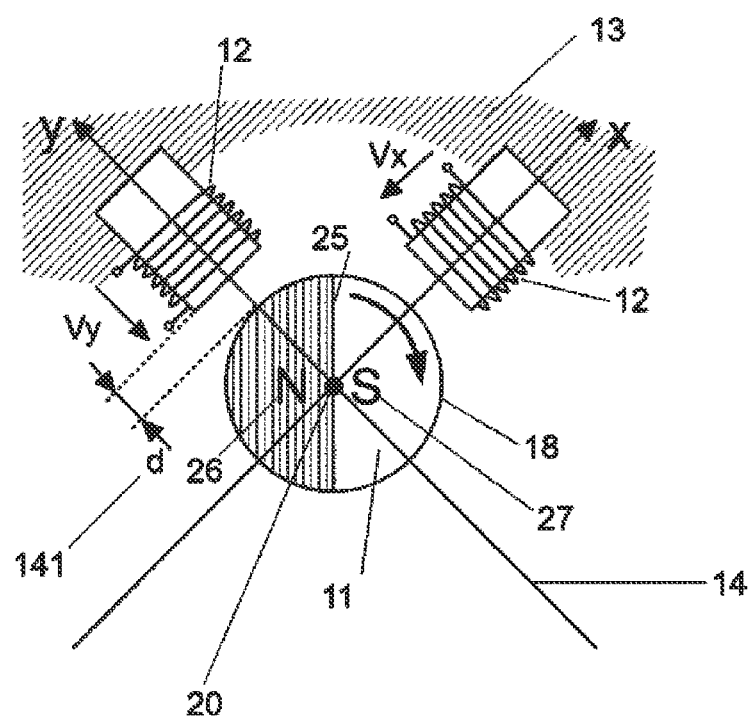
FIG. 2 illustrates an example of a rotor and magnetic field sensors in the radial direction.
Figure 3:
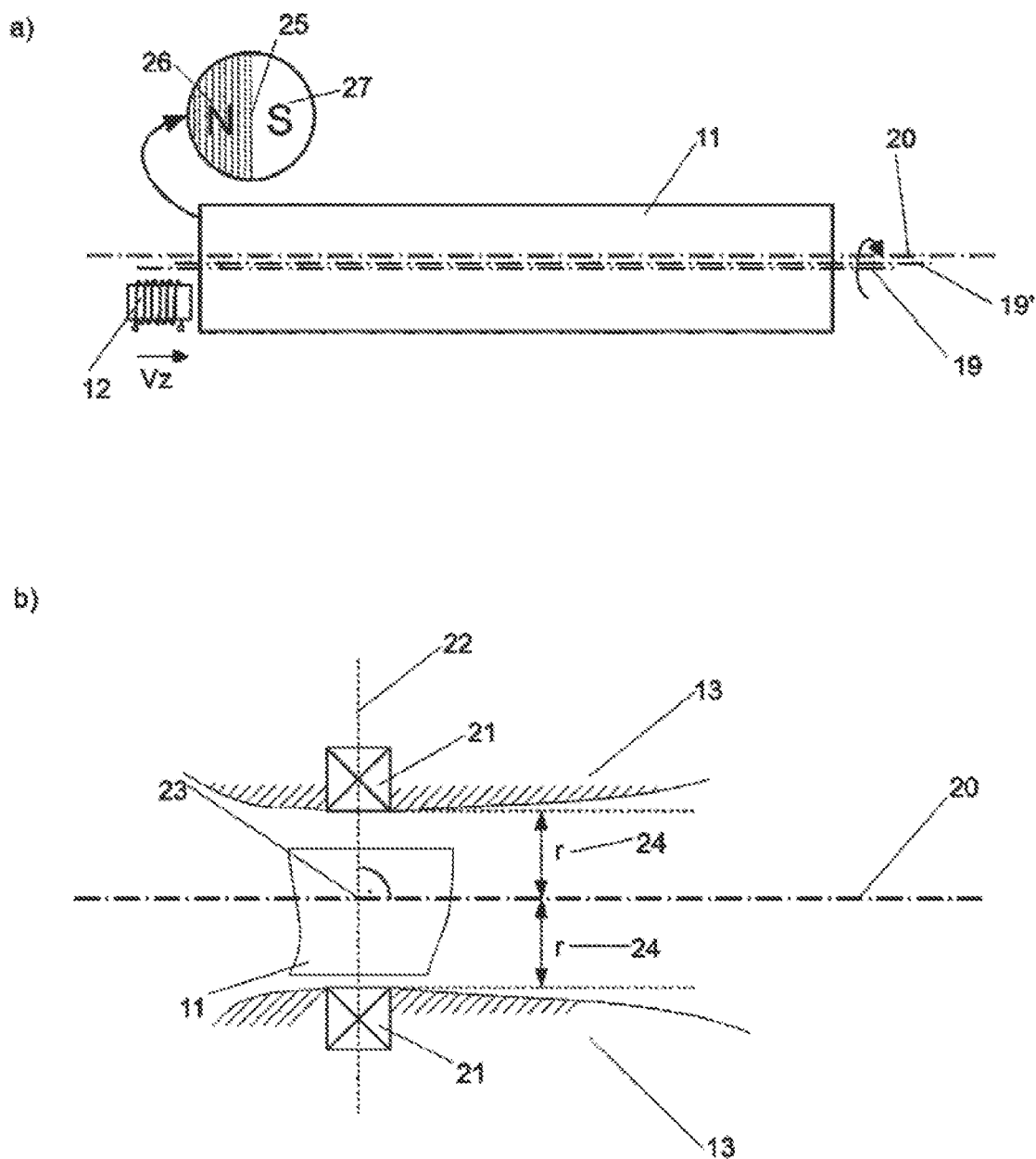
FIG. 3a illustrates an example of a rotor and magnetic field sensors in the axial direction.
FIG. 3b illustrates an axis that is stationary relative to the stator.
Figure 4:
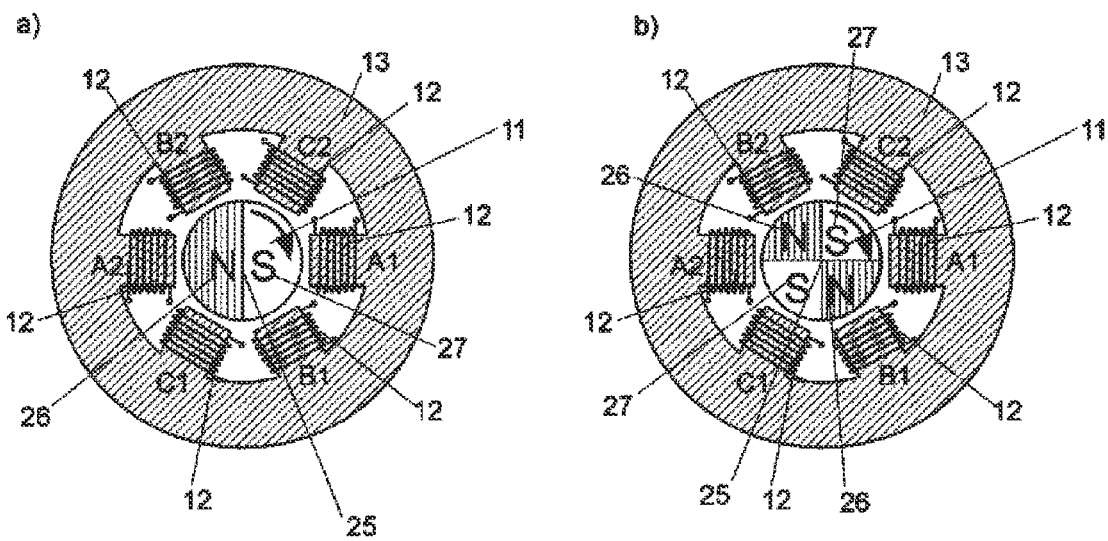
FIG. 4a illustrates an example of magnetic field sensors designed as motor coils having a two-pole rotor.
FIG. 4b illustrates an example of magnetic field sensors designed as motor coils having a four-pole rotor.
FIG. 4c illustrates an example for the definition of a coordinate system fixed to the stator.
Figure 4:
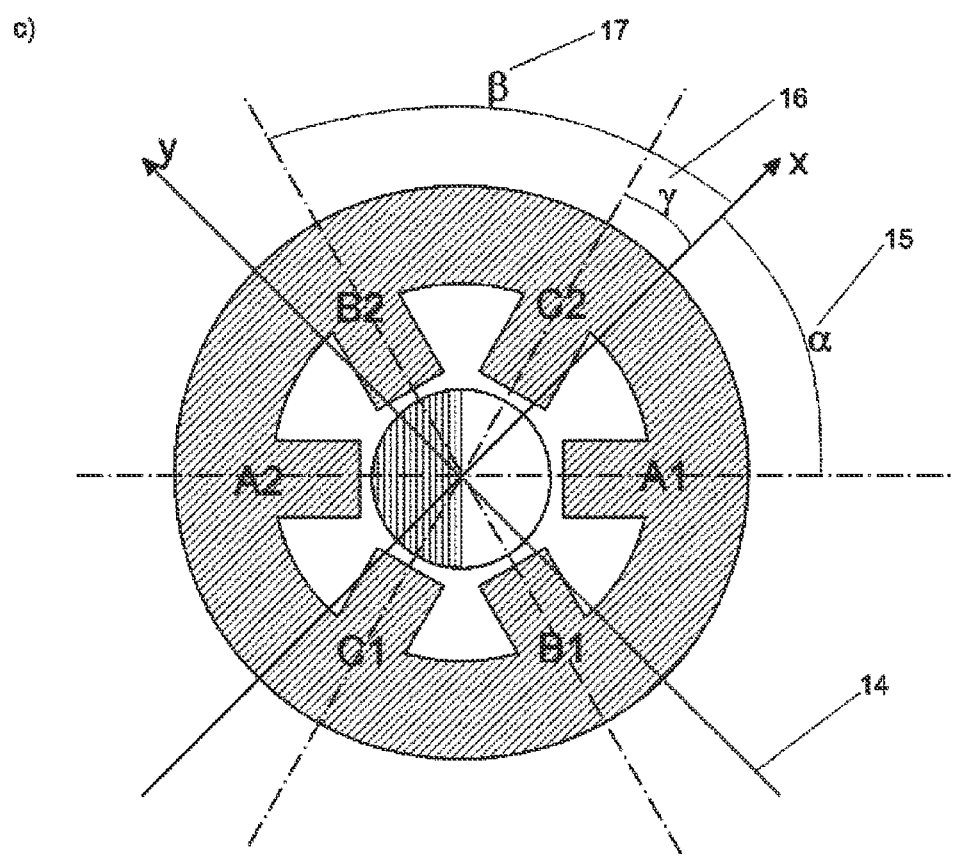

FIG. 2 shows an arrangement that comprises the rotor 11 and magnetic field sensors 12 in a Cartesian coordinate system 14. In principle, the coordinate system 14 is defined as stationary relative to the stator 13, namely in a plane perpendicular to the axis 20, which is stationary relative to the stator. The target position of the rotor axis of rotation is generally placed at the origin of this coordinate system 14. In this example, the magnetic field sensors 12 are each arranged in the axes of the coordinate system 14 such that a rotor-generated magnetic field can penetrate said magnetic field sensors. The rotor 11 contains magnets 25, at least in the axial section of the rotary machine in which the magnetic field sensors 12 are also located, which magnets in this example are designed as permanent magnets having north pole 26 and south pole 27, but can also be electromagnets. Accordingly, an even number of magnetic poles are distributed over the circumference 18 of the rotor 11, so that when the rotor rotates, the magnetic field sensors 12 are exposed to a periodically changing magnetic field. The periodic frequency of said changing magnetic field corresponds to the product of the rotor rotation frequency 171 and the number of pole pairs of the rotor. In this example, the magnetic field sensors 12 are designed as coils, so that a respective voltage $V_x$ or $V_y$, which is proportional to the change in the magnetic flux, is induced in the coils 12 due to the changing magnetic flux. The induced voltage $V_x$ or $V_y$ thus depends both on the rotor rotation frequency 171 and on the distance 141 of the rotor 11 from the respective coil 12, which in this example represents a radial position of the rotor 11 relative to the stationary axis 20.

FIG. 3a shows an arrangement having rotor 11 and magnetic field sensor 12. At least on one end face, the rotor 11 contains a magnet 25 having at least one north pole 26 and one south pole 27, so that the magnetic field sensor 12, which is located at a distance from the rotor 11 in an axial direction, can be penetrated by the magnetic field of said magnet 25, said magnetic field changing during rotation. The magnetic field sensor 12 is designed as a coil 12 in this figure. The coil 12 can also be designed as a motor coil. According to the law of induction, a voltage is induced in the coil 12 said voltage being proportional to the change in the magnetic flux. The induced voltage thus depends both on the rotor rotation frequency 171 and on the distance 140 of the rotor 11 from the coil 12, which indicates an axial position of the rotor relative to the stationary position of the coil 12. FIG. 3a further shows the axis 20 defined as stationary relative to the stator 13. The rotor axis 19' is located in the geometric center of the rotor cross section. The axis of rotation 19 can deviate from the rotor axis 19' and the axis 20 defined as stationary relative to the stator, particularly during rotation due to external forces or imbalances.

FIG. 3b shows a section of the rotor 11 in the region of a possible bearing 21. The bearing can be, for example, a roller bearing, sliding bearing or a magnetic bearing. The position of the axis 20, which is stationary relative to the stator 13, is defined, for example, by the right angle between the bearing plane 22 and the axis 20 and by the point of passage 23 of the axis 20 through the bearing plane 22, the bearing plane being located in the center of the bearing, with the center of the bearing defined by the same spacing, r, 24 to radially opposite elements of the bearing 21.

FIG. 4a shows an axial view of a rotor 11 and stator 13 arrangement which is typical of an electric motor configuration. Shown are the magnetic field sensors 12, which in a motor application can simultaneously serve as drive coils or motor coils, which are designed to generate one or more magnetic fields for generating torque. The coils are labeled as opposed pairs A1-A2, B1-B2, and C1-C3. In a motor application, said pairs can each be electrically connected in series. The rotor 11 contains an arrangement of magnets 25 having a pair of poles consisting of a north pole 26 and a south pole 27.

Analogous to FIG. 4a, FIG. 4b shows an axial view of an arrangement of rotor 11 and stator 13, the arrangement being typical of an electric motor configuration. In contrast to FIG. 4a, the rotor 11 contains an arrangement of magnets having two pairs of poles, that is, two north poles 26 and two south poles 27. In principle, it is also possible to use more than two pairs of rotor poles, each consisting of a north pole 26 and a south pole 27, or more or fewer than the three pairs of coils shown.

FIG. 4c shows an axial view of an arrangement of rotor 11 and stator 13 and the already defined coordinate system 14 with its two mutually orthogonal axes. In addition, the axes defined by the coil pairs A1-A2, B1-B2 and C1-C2 are entered, the axes deviating from the x-axis of the coordinate system 14 due to the angles of rotation $\alpha$ 15, $\beta$ 17 and $\gamma$ 16. Said angles 15, 16 and 17 can be used to convert the distances 141 measured relative to the sensors 12 into coordinates of the coordinate system 14.

Figure 5:
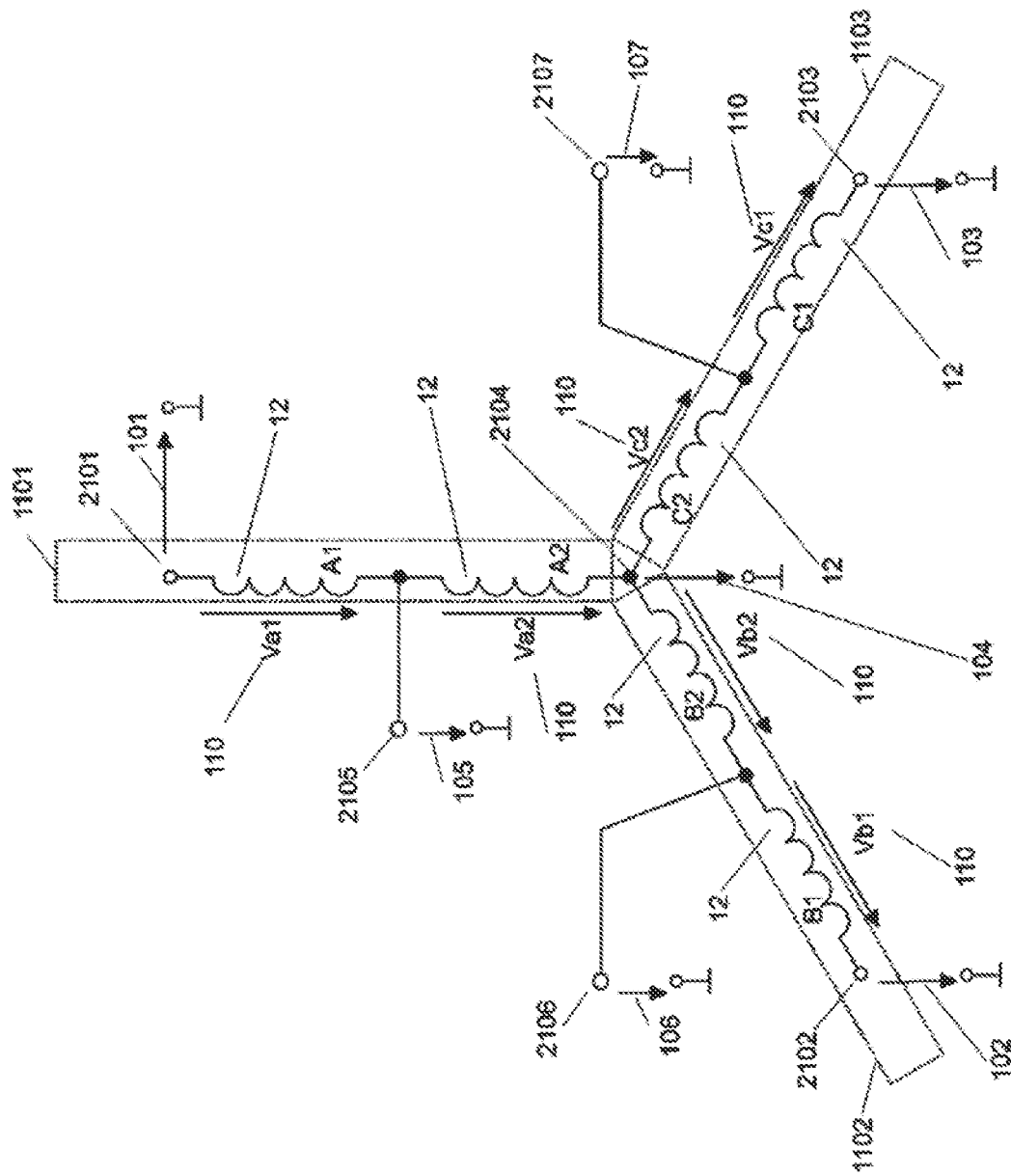
FIG. 5 illustrates an example of the interconnection of motor coils and their use for measuring magnetic fields.

FIG. 5 shows an example of the interconnection of electric motor coils and their use for measuring magnetic fields, that is, as magnetic field sensors 12. A star connection is depicted, with the motor electrically connected to the phase connections 2101, 2102 and 2103 and the neutral point connection 2104 for motor operation. Each phase connection 2101, 2102 and 2103 is the connection for an electrical phase 1101, 1102 and 1103 of the motor, each consisting of a pair of coils A1-A2, B1-B2 and C1-C2. The phases 1101, 1102 and 1103 are electrically connected to one another in the neutral point connection 2104. In addition, the center tap terminals 2105, 2106 and 2107 are defined. Furthermore, the voltages 101, 102, 103, 104, 105, 106 and 107 are each measured against ground, for example. In addition to the voltages or currents impressed via the phase connections 1101, 1102 and 1103 by a motor controller, when the rotor 11 rotates, voltages are induced in the coils 12, the voltages dropping across the coils 12 A1, A2, B1, B2 and C1 and C2. This representation thus shows an example of an electrical interconnection of the magnetic field sensors 12 when said sensors are designed as motor coils. The motor coils are therefore part of measuring device 1. The voltages 101, 102, 103, 104, 105, 106, 107 and the total voltages 110, Va1, Va2, Vb1, Vb2, Vc1 and Vc2 dropping across the coils 12 can be made accessible for the subsequent processing by, for example, electrical connectors and terminals and optionally measuring amplifiers, level converters or impedance converters.

Figure 6:
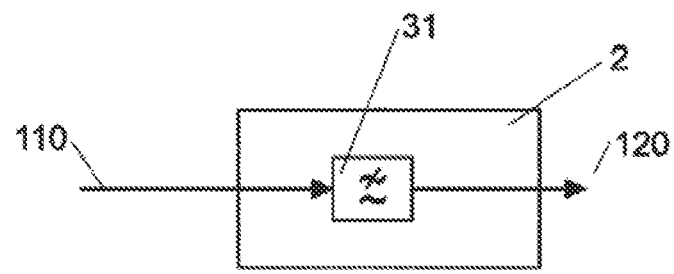
FIG. 6a illustrates an example of the pre-processing of the magnetic field sensor signals using frequency-selective filtering.
FIG. 6b illustrates an example of the pre-processing of the magnetic field sensor signals using frequency-selective filtering and signal combination.
FIG. 6c illustrates an example of the pre-processing of the magnetic field sensor signals using signal combination.
Figure 6:
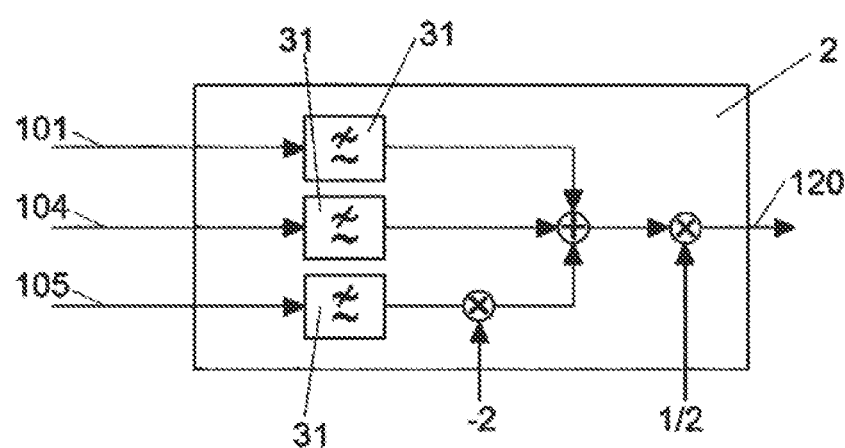
Figure 6:
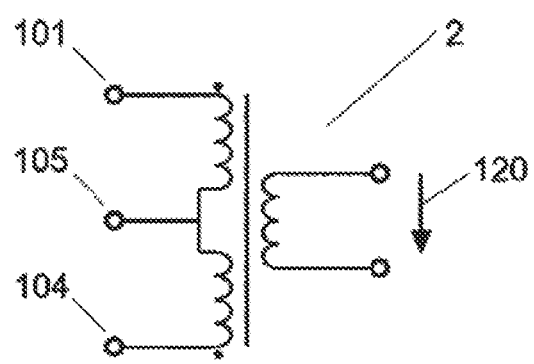
Figure 7:
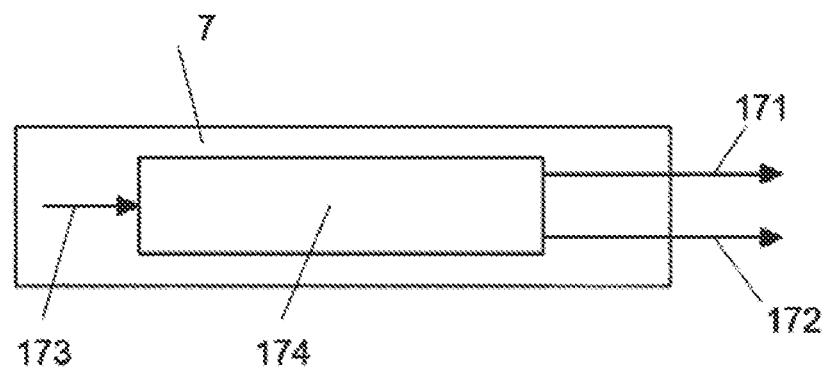
FIG. 7a illustrates an example of determining the rotor rotation frequency and the rotor rotation angle with the aid of a counter assembly.
FIG. 7b illustrates an example of determining the rotor rotation frequency and the rotor rotation angle with the aid of the motor controller.
Figure 7:
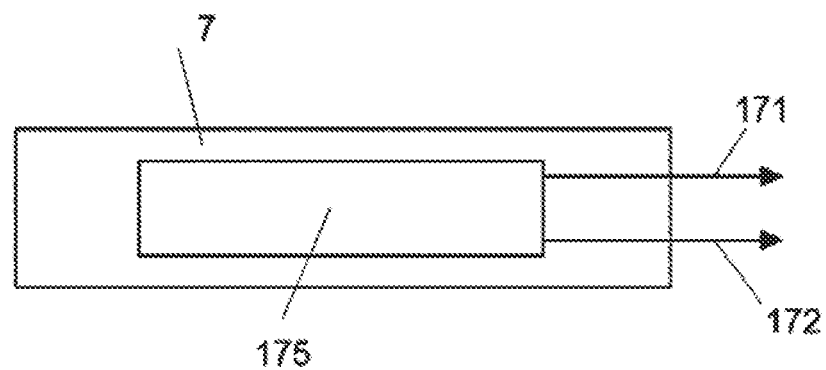
Figure 8:
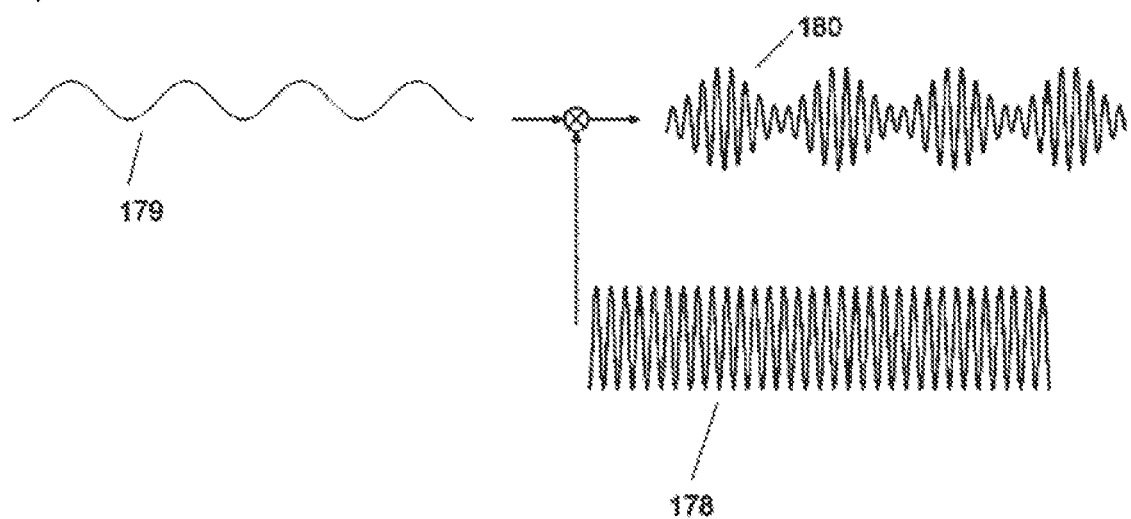
FIG. 8a illustrates a signal example of an amplitude modulation in the time domain.
FIG. 8b illustrates a signal example of an amplitude modulation in the frequency domain.
Figure 8:
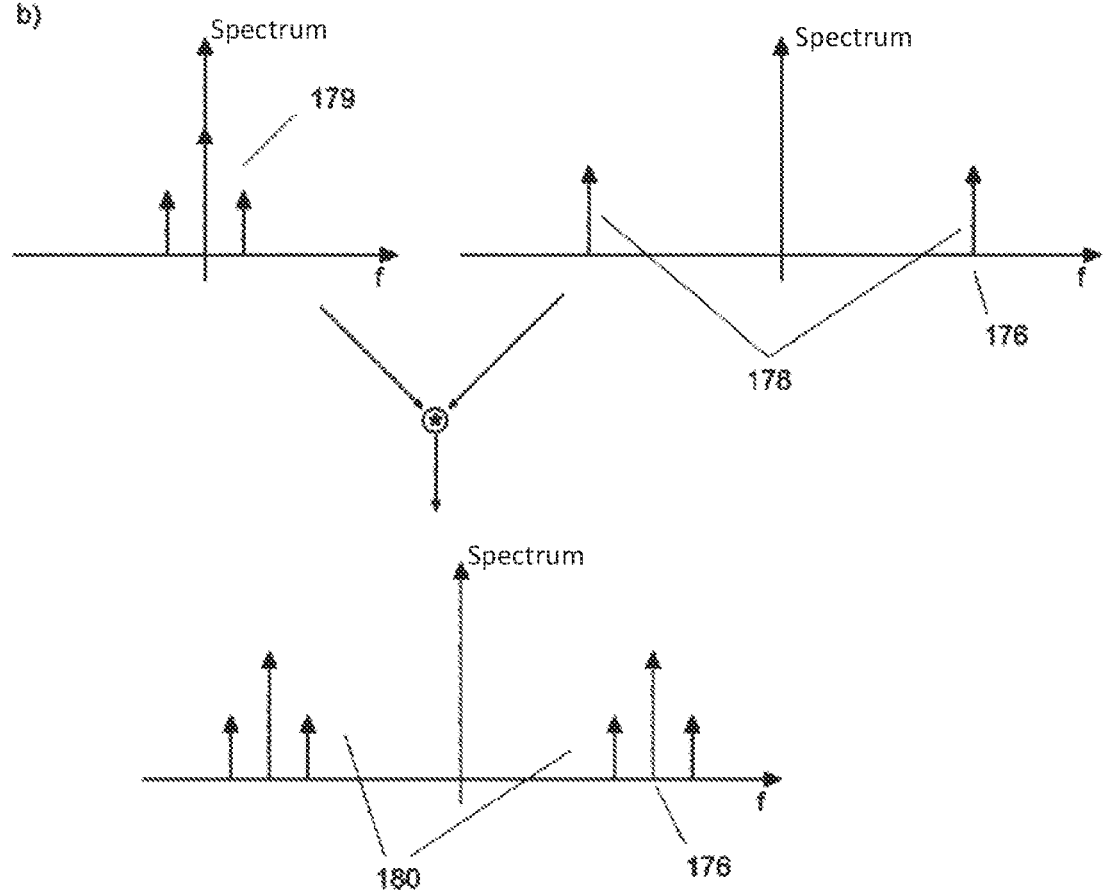
Figure 9:
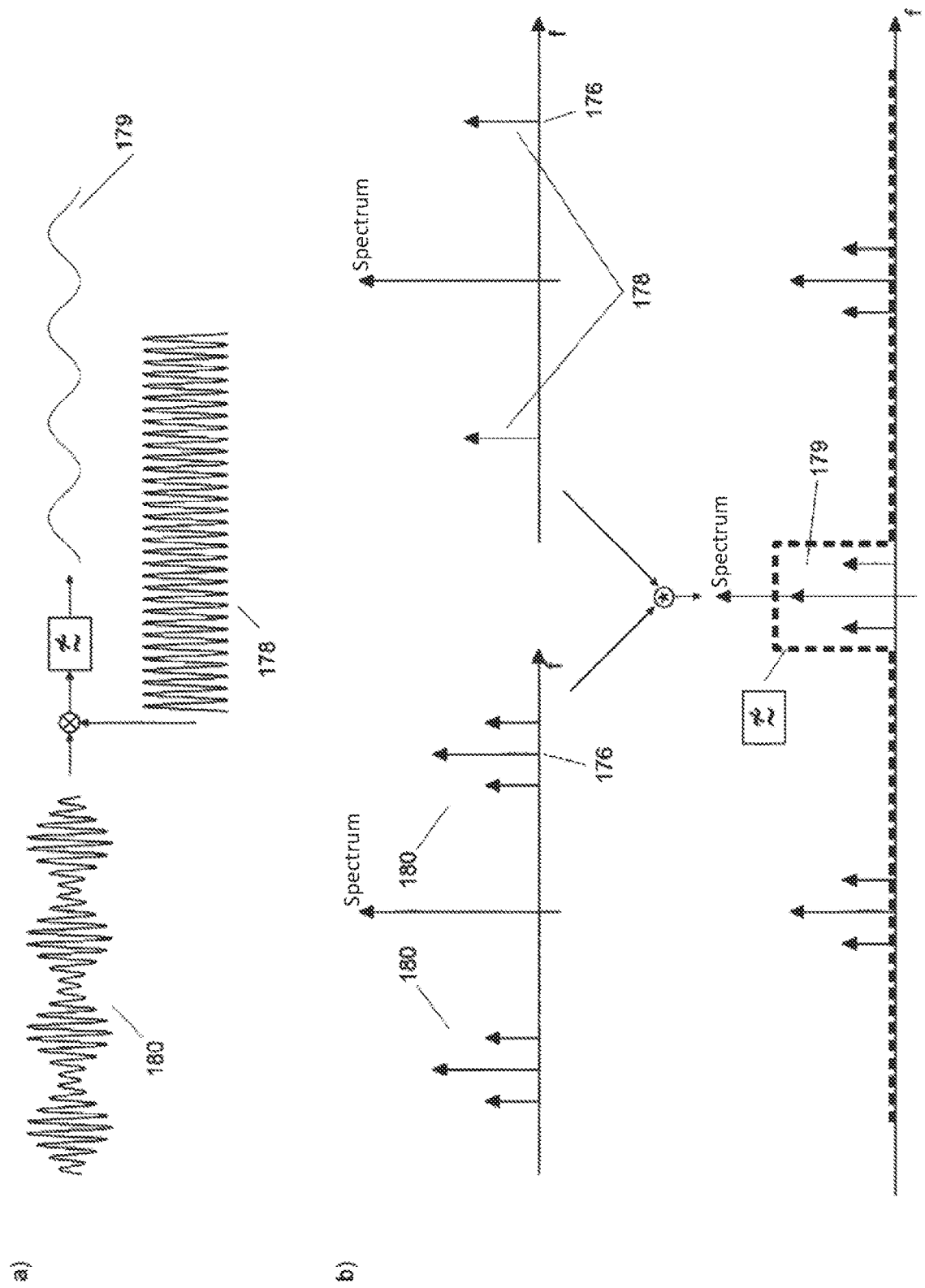
FIG. 9a illustrates a signal example of an amplitude demodulation in the time domain.
FIG. 9b illustrates a signal example of an amplitude demodulation in the frequency domain.

The signal conditioning 2 is shown in the parts of FIG. 6.

FIG. 6a shows a signal conditioner 2, which filters a coil voltage 110 using a filter 31, which is designed as a low-pass filter. The low-pass filtering removes higher-frequency signal components from coil voltage signal 110 that are irrelevant for determining the rotor position. For example, the irrelevant signal components can be the pulse-width modulated (PWM) signals from the motor controller, which can have high-frequency switching frequencies of, for example, 4 kHz or 8 kHz and the harmonic components of which can reach into the MHz range. A low-pass filter, which is designed to suppress the pulse-width-modulated signal components of the motor controller, can have a stopband frequency of 3.9 kHz, for example, with the stopband frequency being the frequency above which signal components in the signal are suppressed. The passband frequency of such a low-pass filter can be set, for example, such that the signal components relevant for determining the rotor position can pass through the filter with little or no attenuation. In such an example, the minimum passband frequency results from the sum of the carrier oscillation frequency 176 and the maximum frequency of the modulation signal 179. Alternatively, another filter 31 can also be used here, for example, a bandpass filter, with the bandpass filter being able to have the passband frequency of the described low-pass filter as the upper passband frequency and the stopband frequency of the described low-pass filter as the upper stopband frequency. In such an example, the lower passband frequency of the bandpass results from the carrier oscillation frequency 176 minus the maximum frequency of the modulation signal 179. The lower stop frequency must be lower than the lower passband frequency, but can otherwise be chosen freely, for example.

FIG. 6b shows the signal conditioning 2 by combining a plurality of measurement signals. For example, the voltage of phase A 101, the voltage at the neutral point 104 and the voltage at the center tap A 105 are combined. All three voltages 101, 104, 105 are measured against ground, for example. First, all three voltage signals 101, 104 and 105 are filtered using a filter 31, which is designed as a low-pass filter, to remove the PWM signal components, before said signal components are then added up in a weighted manner. Motor signal components can be removed from the voltage signal using this circuit, for example, since the difference between the voltages Va1-Va2 introduced in FIG. 5 is determined with this circuit. Assuming that coils A1 and A2 are identical, both voltages contain a voltage Vm due to the motor activation and the voltage Vp due to the modulated rotor position signal, said voltages, however, having different signs due to the opposite arrangement of coils A1 and A2. The circuit shown in FIG. 6b thus calculates voltage $$(Va1-Va2)/2=((Vm+Vp)-(Vm-Vp))/2=2Vp/2=Vp.$$

The result of the equation also holds in the case of a two-pole rotor.

This example shows that the combination of a plurality of coil voltages 110 can advantageously be used in certain specific embodiments to reduce the signal components that are not relevant for determining the rotor position. In the conditioned signal 120, the signal components associated with the motor controller are suppressed.

FIG. 6c shows a practical implementation possibility of the signal conditioner 2 shown in FIG. 6b with a transformer. Active computing circuits with operational amplifiers, which are known from the literature, offer an alternative to a transformer circuit.

FIG. 7a shows a possible implementation of a device 7 for providing the rotor rotation frequency 171 and optionally the rotor rotation angle 172. As an essential component of the device 7, a counter assembly 174 is shown by way of example, the counter assembly, for example, incrementing an internal counter in a regular cycle. Said counter assembly 174 receives a signal, for example, a voltage pulse, which is generated by a keyphasor 173 at an input. For example, said voltage pulse generated by the keyphasor 173 can be converted by further assemblies into a voltage pulse which has a uniform predetermined voltage, for example, 5V, and for example, also a uniform length, for example, 50 ps. Said voltage pulse is generated by the keyphasor 173 whenever a keyphasor groove passes the keyphasor 173 during a revolution of the rotor 11. Therefore, as many voltage pulses are generated per rotor revolution as there are keyphasor grooves on the rotor. The further processing of the voltage pulse for the case in which exactly one keyphasor groove is arranged on the rotor 11 is explained as an example. In counter assembly 174, the internal counter is reset to zero, for example, on a rising signal edge of the voltage pulse, and the counting process, which includes clocked incrementing of the counter, is started. The clock frequency is set such that a large number of increments are carried out per rotor revolution, even at maximum speed. When the same edge of the subsequent voltage pulse arrives, the current counter value is saved, the counter is reset to zero and the counting process restarts. The rotor rotation frequency 171 is determined by dividing the clock frequency by the stored counter value. To estimate the rotor rotation angle during the subsequent revolution, for example, the respective current counter value is divided by the stored counter value and multiplied by 360°. Rotor rotation frequency 171 and rotor rotation angle 172 are made available at the output of device 7.

FIG. 7b shows an alternative device 7 for providing the rotor rotation frequency 171 and optionally the rotor rotation angle 172, which can be implemented in some motors. In this case, for example, the rotor rotation frequency 171 and the rotor rotation angle 172 are already present in the motor and are made available by the motor controller 175.

FIG. 8a shows a signal example for the generation of an amplitude-modulated signal 180 in the time domain. The amplitude-modulated signal 180 results from the multiplication of a carrier oscillation 178 by a modulation signal 179. The frequency of the carrier oscillation 178 is referred to as the carrier oscillation frequency 176. The carrier oscillation frequency 176 can be seen in the amplitude-modulated signal 180. In addition, the amplitude of the amplitude-modulated signal 180 fluctuates synchronously with the modulation signal 179. In the rotary machine disclosed, the modulation signal 179 corresponds to the distance 141 between a magnetic field sensor 12 and the rotor 11. The carrier oscillation signal is generated in the magnetic field sensors 12 by the changes in the magnetic flux in the magnetic field sensors 12 caused by the magnetic rotor poles 26, 27.

FIG. 8b shows a signal example for the generation of an amplitude-modulated signal 180 in the frequency domain. The spectrum, that is, the Fourier transform, of the modulation signal 179 is convolved with the spectrum, that is, the Fourier transform of the carrier oscillation 178. The result is the spectrum, that is, the Fourier transform of the amplitude-modulated signal 180. The spectrum of the amplitude-modulated signal 180 shows the spectrum of the modulation signal 179 respectively shifted by the carrier oscillation frequency 176 to the left, that is, towards negative frequencies, and by the carrier oscillation frequency 176 to the right, that is, towards positive frequencies.

FIG. 9a shows a signal example for the amplitude modulation of an amplitude-modulated signal 180 in the time domain. The amplitude-modulated signal 180 is multiplied by the carrier oscillation 178 and then filtered with a low-pass filter. The result is the demodulated signal 179. The necessity of the low-pass filter becomes clear in FIG. 9b.

FIG. 9b shows a signal example for the amplitude modulation of an amplitude-modulated signal 180 in the frequency domain. The amplitude-modulated signal 180, the components of which are arranged around the carrier oscillation frequency 176, is convolved with the spectrum, that is, the Fourier transform, of the carrier oscillation 178. As a result, the spectrum of the modulation signal (see FIG. 8b) becomes visible in three regions. In order to suppress the two spectral regions that are not at 0 Hz and to recover the spectrum of the modulation signal 179, the signal is filtered with a low-pass filter (dashed area).

Figure 10:
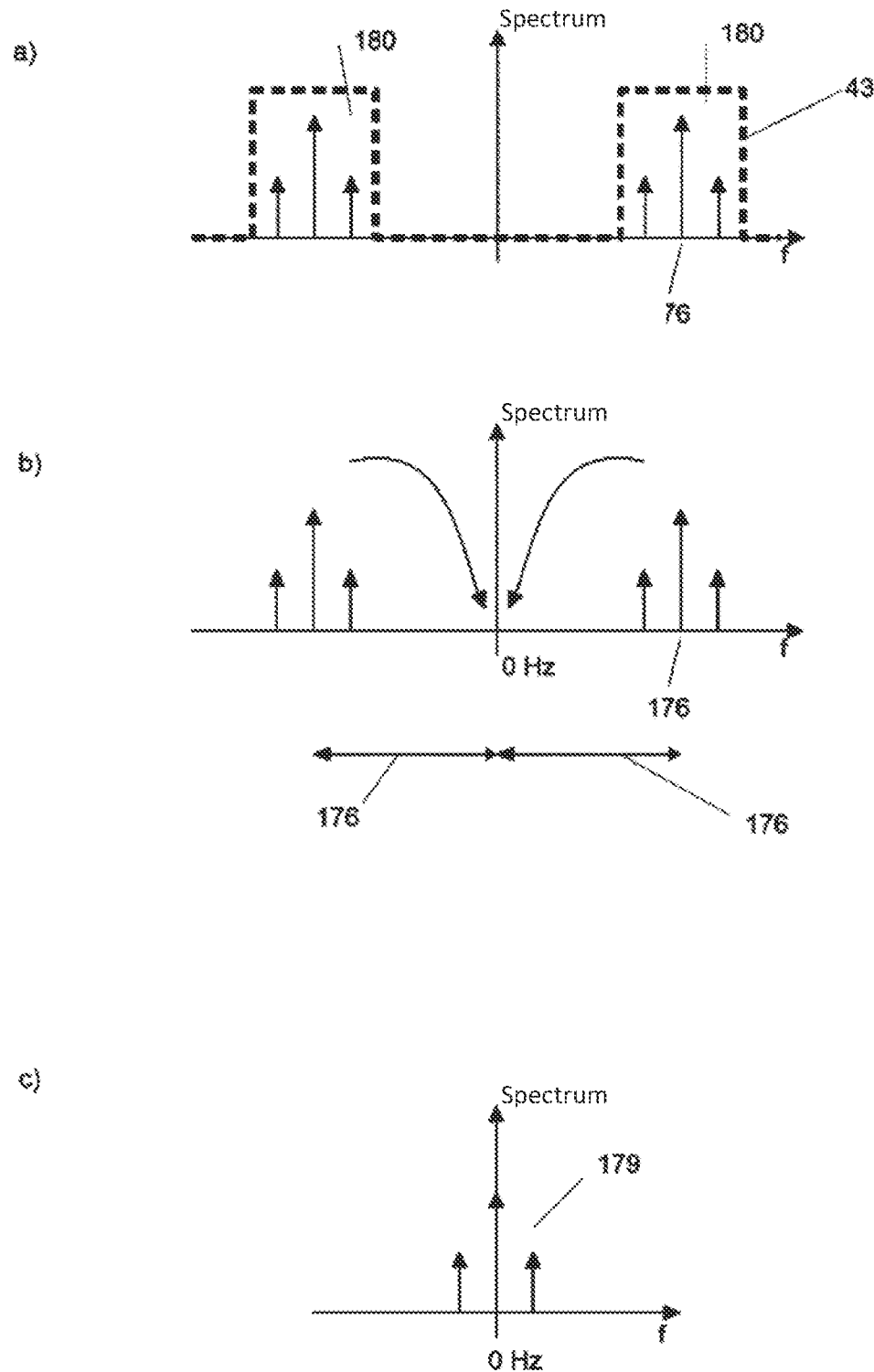
FIG. 10a illustrates an example of masking in the frequency domain.
FIG. 10b illustrates an example of frequency shift in the frequency domain.
FIG. 10c illustrates an example of demodulated signal in the frequency domain.

FIG. 10 shows an example of a demodulation method in the frequency domain.

FIG. 10a shows the spectrum of the amplitude-modulated signal 180. Said spectrum is arranged around the carrier oscillation frequency 176 in each case. For demodulation in the frequency domain, all signal components, that is, Fourier coefficients, which do not belong to the amplitude-modulated signal are masked by the masking device 43, that is, set to zero.

The actual demodulation is shown in FIG. 10b. The signal components remaining after masking are shifted from the original position to the frequency 0 Hz, that is, copied and deleted at the original location. The shift occurs by a frequency amount that corresponds to the carrier oscillation frequency 176. Coefficients in the same place after the shift are added.

FIG. 10c shows the spectrum resulting from this procedure. Said spectrum corresponds to the spectrum of the modulation signal 179.

Figure 11:
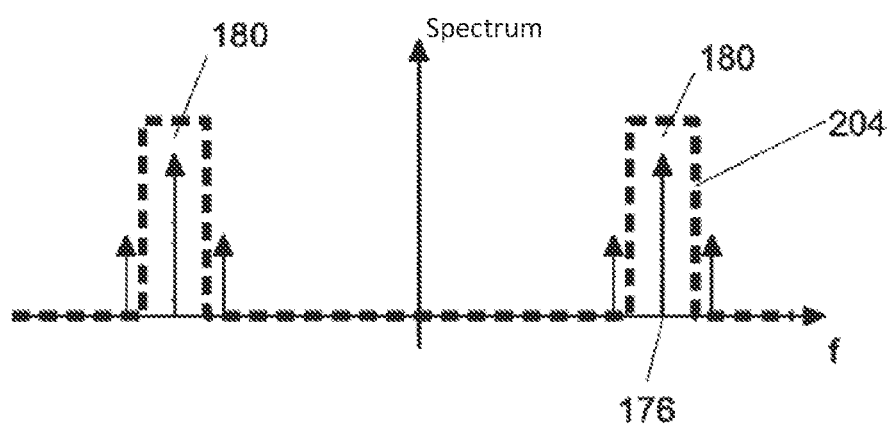
FIG. 11 illustrates an example of carrier synthesis by masking in the frequency domain.
Figure 12:
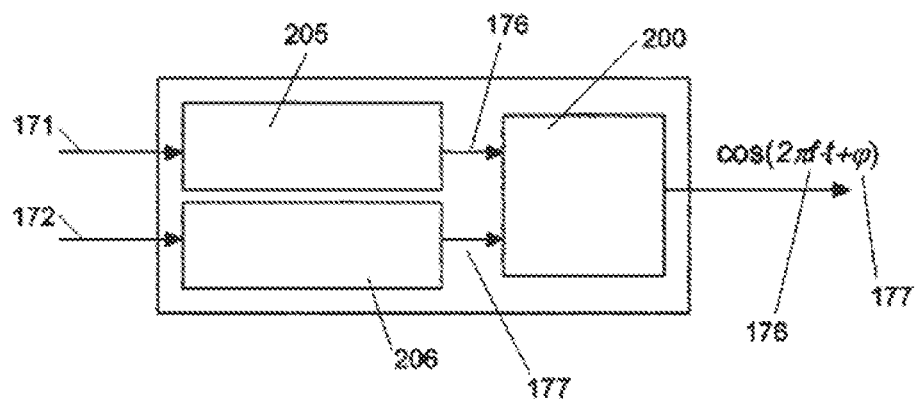
FIG. 12a illustrates an example of carrier synthesis for amplitude demodulation with the aid of an oscillator circuit.
FIG. 12b illustrates an example of carrier synthesis for amplitude demodulation with the aid of Fourier transformation.
Figure 12:
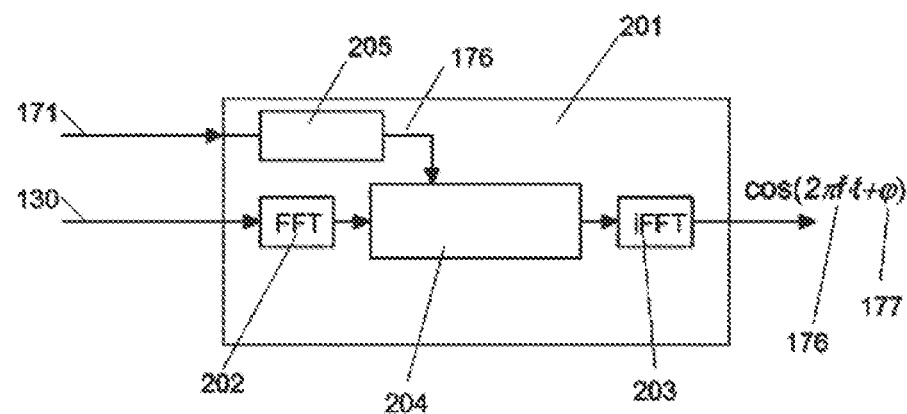

FIG. 11 shows an example of software-based carrier synthesis 201 by masking in the frequency domain. For this purpose, the amplitude-modulated signal 180 is masked in the frequency domain such that all signal components that do not belong to the carrier oscillation 178, that is, have frequency components that do not have the carrier oscillation frequency 176, are set to zero by the device for peak detection and masking 204. The signal masked in this way is transformed into the time domain as part of the software-based carrier synthesis 201. If the carrier oscillation frequency 176 is not known, it can be estimated by the device 204, for example, by peak detection.

FIG. 12a shows a possibility of generating a carrier oscillation using an electronic assembly for carrier synthesis 200. Such an assembly 200 can be an electronic oscillator circuit, for example, in which a carrier oscillation 178 is generated from the rotor rotation frequency 171 and the rotor rotation angle 172 using the specifications for the frequency and phase position. As an alternative thereto, the carrier synthesis 200 can take place with the aid of a microcontroller or computer, in which a signal stored in a memory is retrieved and converted into an electrical voltage signal using a digital-to-analog converter. In certain embodiments, the advantage of this method is greater flexibility and easier configurability. The carrier oscillation frequency 176 to be generated by the carrier synthesis 200 results from the product of the rotor rotation frequency and the number of pole pairs of the rotor. It is calculated in the assembly 205 for calculating the carrier frequency 176. The phase position 177 to be generated is calculated in the assembly 206 for calculating the phase position 177. It must be individually adjusted for each magnetic field sensor signal or signal to be demodulated. It depends on the positions of the magnetic field sensor and the fixed stator reference point for the rotor rotation angle, the current position of the rotor fixed reference point for the rotor rotation angle and the number of pole pairs of the rotor.

FIG. 12b shows an example of a software-based carrier synthesis 201 using the discrete Fourier transformation. For this purpose, a signal 130 converted into the digital domain is transformed into the frequency domain, for example, by the FFT transformation unit 202, which is designed to carry out a fast Fourier transformation (FFT). The transformed signal is passed to a peak detection and masking unit 204, which is designed to detect peaks in the Fourier transform and to mask, that is, set to zero, frequency bands or individual frequencies. Said unit 204 masks all ranges of the Fourier transform that are not in a predefined range around the carrier oscillation frequency 176. The carrier oscillation frequency 176 results from the product of the rotor rotation frequency 171 and the number of pole pairs of the rotor. The masked signal is transformed into the time domain in the iFFT unit, which is designed to carry out an inverse Fourier transformation (iFFT). The result is a carrier oscillation signal having the carrier oscillation frequency 176 and phase position 177 suitable for the demodulation.

Figure 13:
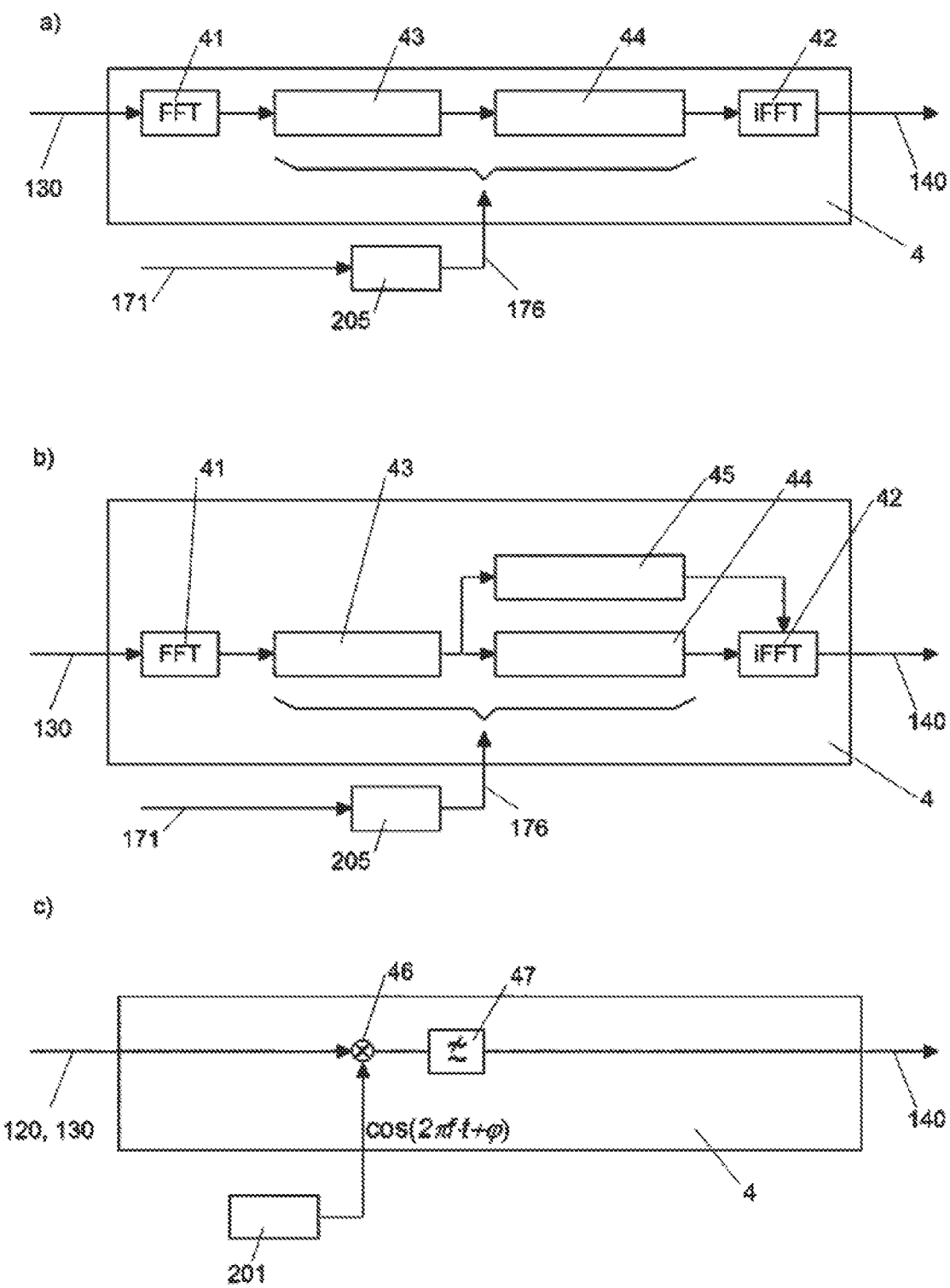
FIG. 13a illustrates an example of demodulation using rotor rotation frequency in the frequency domain without rotor rotation angle.
FIG. 13b illustrates an example of demodulation using rotor rotation frequency in the frequency domain with rotor rotation angle.
FIG. 13c illustrates an example of demodulation with rotor rotation frequency and rotor rotation angle in the time domain.

FIG. 13 shows various examples of the demodulator in the time and frequency domain.

FIG. 13a shows an example of the demodulator 4 in the frequency domain with the rotor rotation frequency 171 and without the rotor rotation angle 172. In this case, the digitally present signal 130 is transformed into the frequency domain with the aid of the fast Fourier transformation (FFT) 41. A masking 43 is carried out in the Fourier transform, that is, all frequency components which are not in the vicinity of the carrier oscillation frequency 176 are set to zero. The carrier oscillation frequency 176 is made available by the unit 205 for calculating the carrier oscillation frequency 176. It results from the product of the rotor rotation frequency 171 and the number of pole pairs of the rotor. Care must be taken to ensure that the masking 43 is to be carried out both for frequency support points which correspond to positive frequencies and for frequency support points which correspond to negative frequencies. Furthermore, there is a shift 44 of the remaining frequency components by the amount of the carrier oscillation frequency 176 in the direction of the frequency 0 Hz. In this case, shifted frequencies are complexly added to frequency components that are already around 0 Hz. The resulting signal is transformed back into the time domain with the aid of an inverse fast Fourier transformation. The resulting signal 140 does not contain correct phase information and therefore cannot be used to calculate the rotor position. However, said signal's power can be used to estimate the current vibration level of the rotor.

In addition to the processing stages shown in FIG. 13a, a phase correction is performed in the example of FIG. 13b. The phase correction of each of the Fourier coefficients shifted in the direction of 0 Hz is carried out such that the amount of the corrected phase results from the amount of the difference between the uncorrected phase and the phase value of the carrier oscillation frequency 176.

FIG. 13c shows an example for the demodulation with carrier oscillation frequency 176 and phase position 177 in the time domain. Here, the digitally available signal 130 is demodulated with the cosine signal synthesized by the assembly of the carrier synthesis 201, which cosine signal has the carrier oscillation frequency 176 and the estimated phase position 177, with the aid of a multiplier 46 and subsequent low-pass filtering. The low-pass filter can be implemented in the time domain as a digital filter or in the frequency domain by masking frequency components to be removed.

Figure 14:
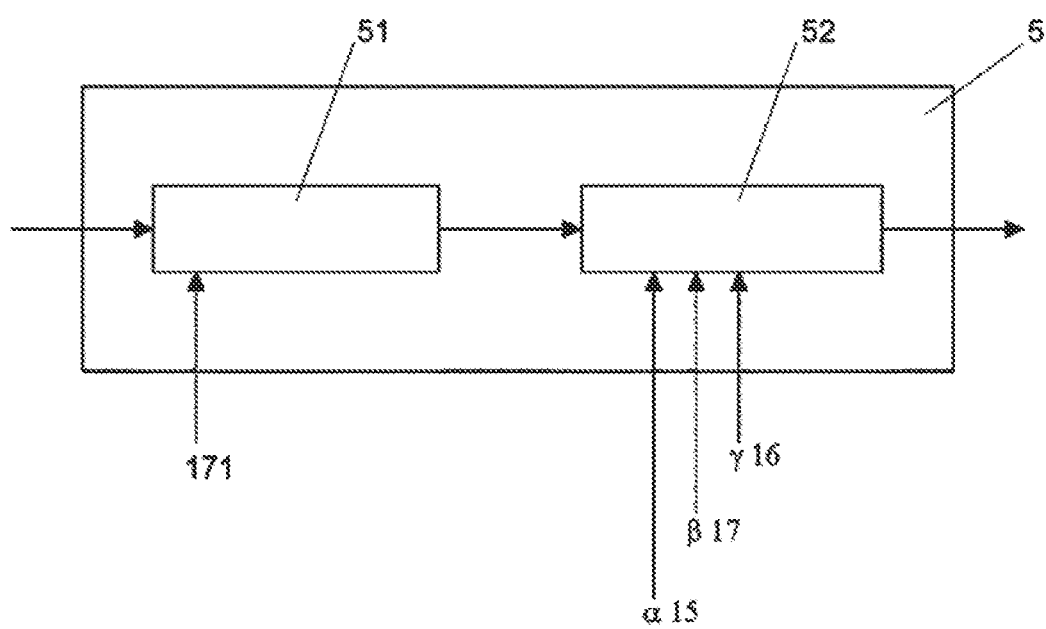
FIG. 14: the mapping of the demodulated magnetic field sensor signals onto a coordinate system.

FIG. 14 shows an example of the device 5 for calculating the rotor position. The device 5 contains a speed-dependent scaling 51 as a first processing stage, which scaling calculates a speed-dependent correction factor using the rotor rotation frequency 171 and the information on the number of pole pairs of the rotor. Said correction factor takes into account that if, for example, the magnetic field sensors are designed as coils, the induced voltage is proportional to the change in the magnetic flux. However, the change in the magnetic flux is directly dependent on the rotor rotation frequency 171 so that this effect must be eliminated when calculating the distance between a magnetic field sensor and the rotor. The speed-dependent scaling 51 can be designed, for example, as a table or a characteristic diagram and can be implemented in a computer or microprocessor.

The distance values corrected in this way are then used to determine the rotor position. For this purpose, a deviation from a predetermined target value is calculated for each distance value by subtracting the predefined target value from the corrected distance values. Using the known angles α 15, ß 17 and γ 16, which indicate the angular offset of the axes defined by the magnetic field sensors 12 relative to the coordinate system 14, the position of the rotor can be mapped from the respective magnetic field sensor axis to the coordinate axes of the coordinate system 14 using trigonometric relationships. The coordinates in the coordinate system 14 resulting from the various magnetic field sensors 12 can be combined, for example, by averaging.

Figure 15:
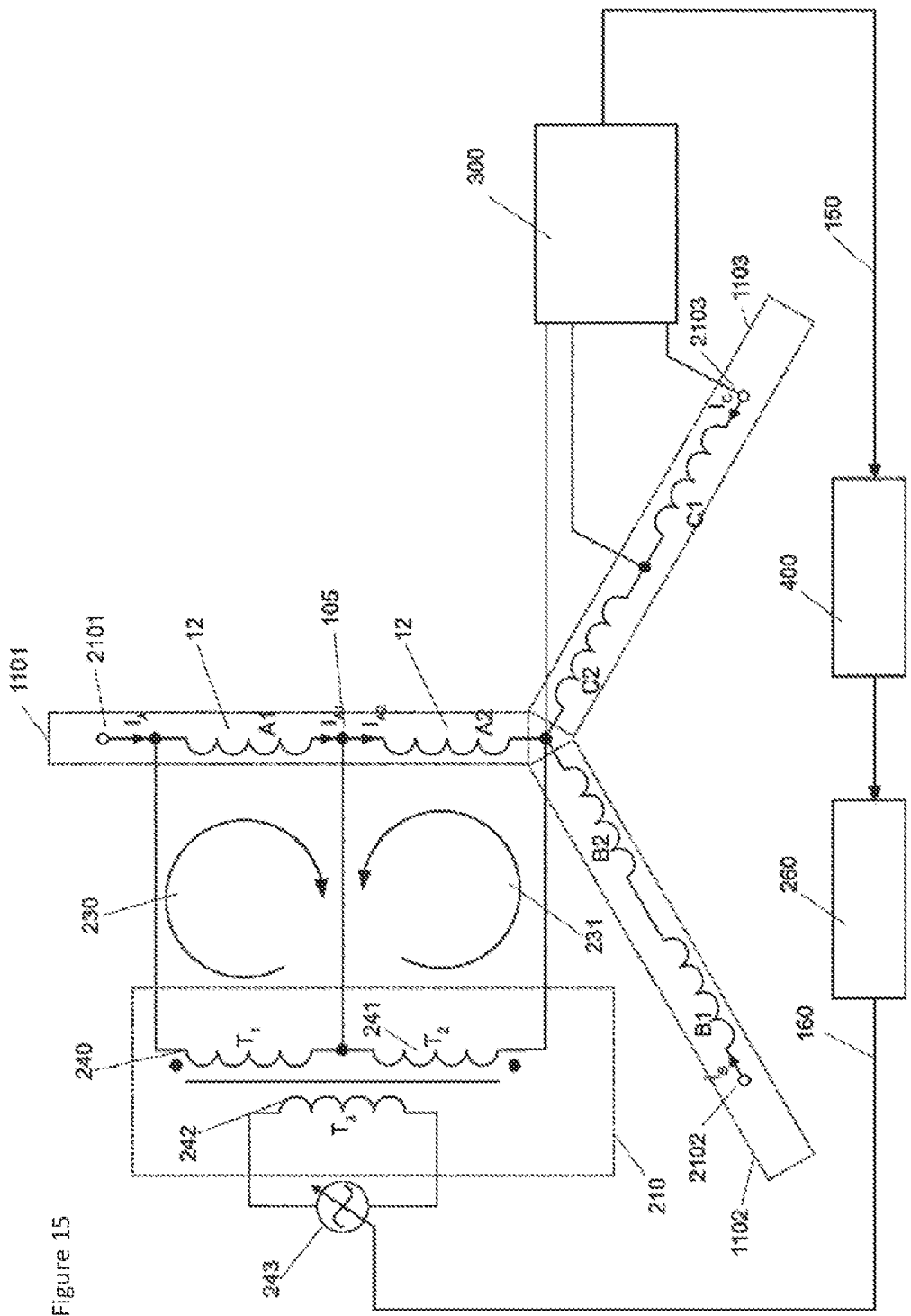
FIG. 15 illustrates an example of using the rotor position in a regulated rotor position system.
Figure 16:
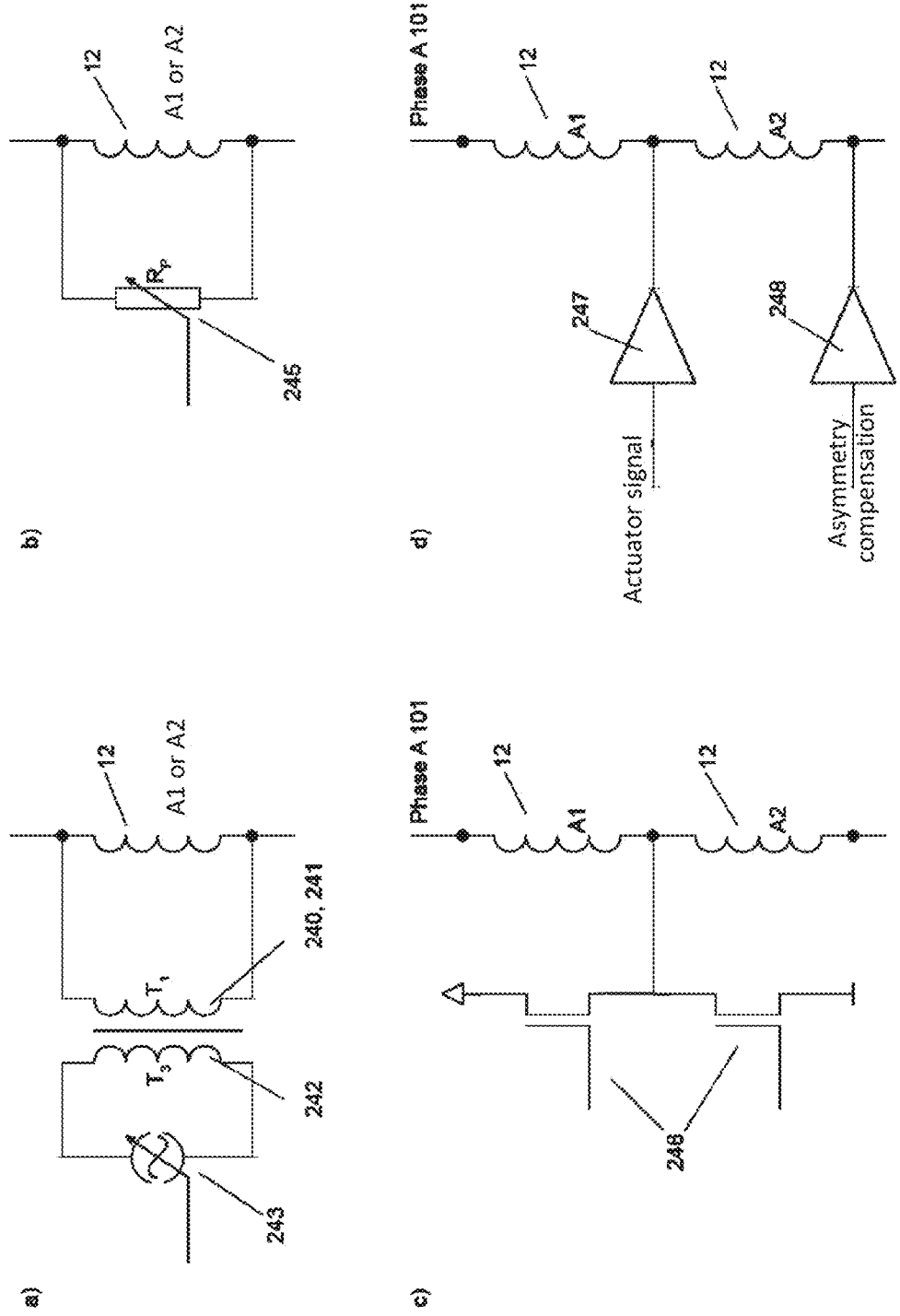
FIG. 16a illustrates a coupling an actuator signal into a motor coil.
FIG. 16b illustrates a modulation of the actuator force in a motor coil with a regulated bypass.
FIG. 16c illustrates impressing an actuator signal in the center tap of a motor phase by means of an additional half bridge.
FIG. 16d illustrates an impressing an actuator signal in the center tap of a motor phase and impressing a compensation signal to suppress the influence of the motor driver by the actuator signal.
Figure 17:
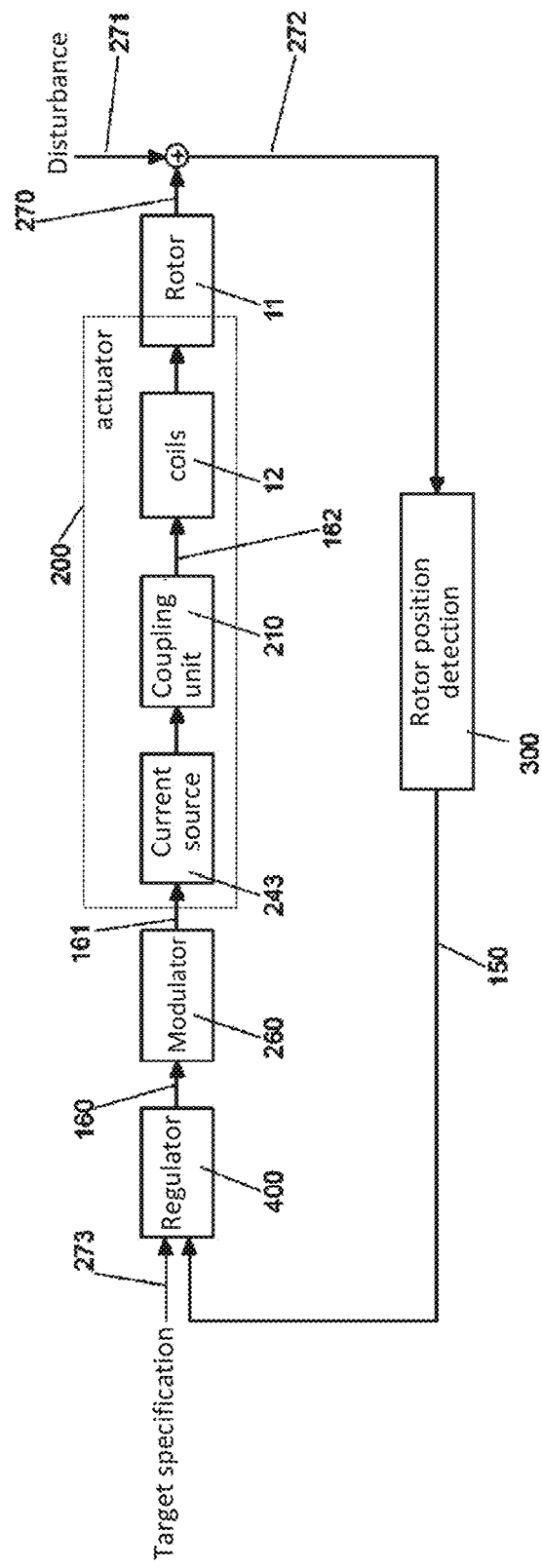
FIG. 17 illustrates a general control loop to compensate for rotor position disturbances.
Figure 18:
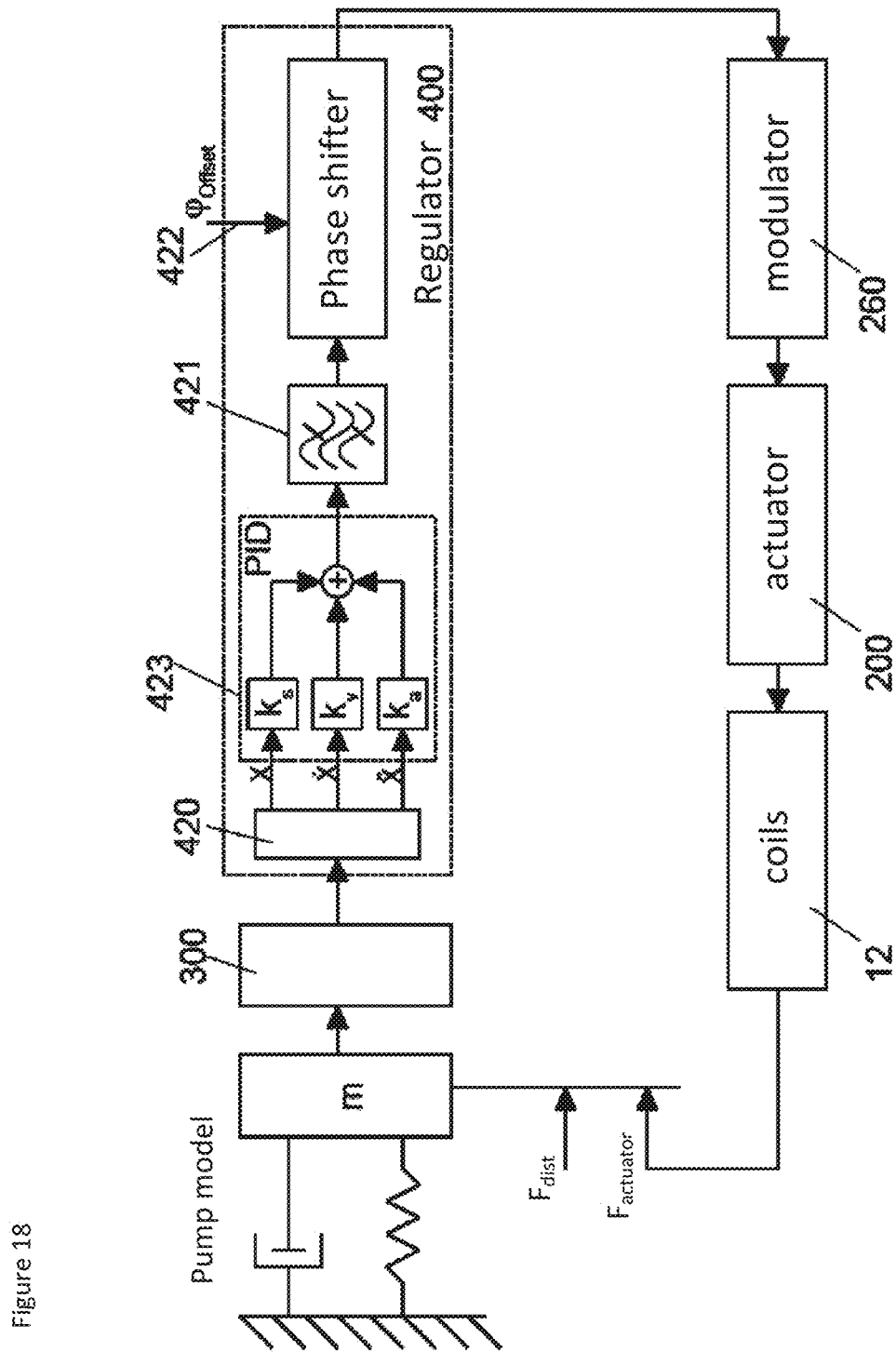
FIG. 18 illustrates a model for compensating for disturbing forces through feedback via PID controller and phase shifter.
Figure 19:
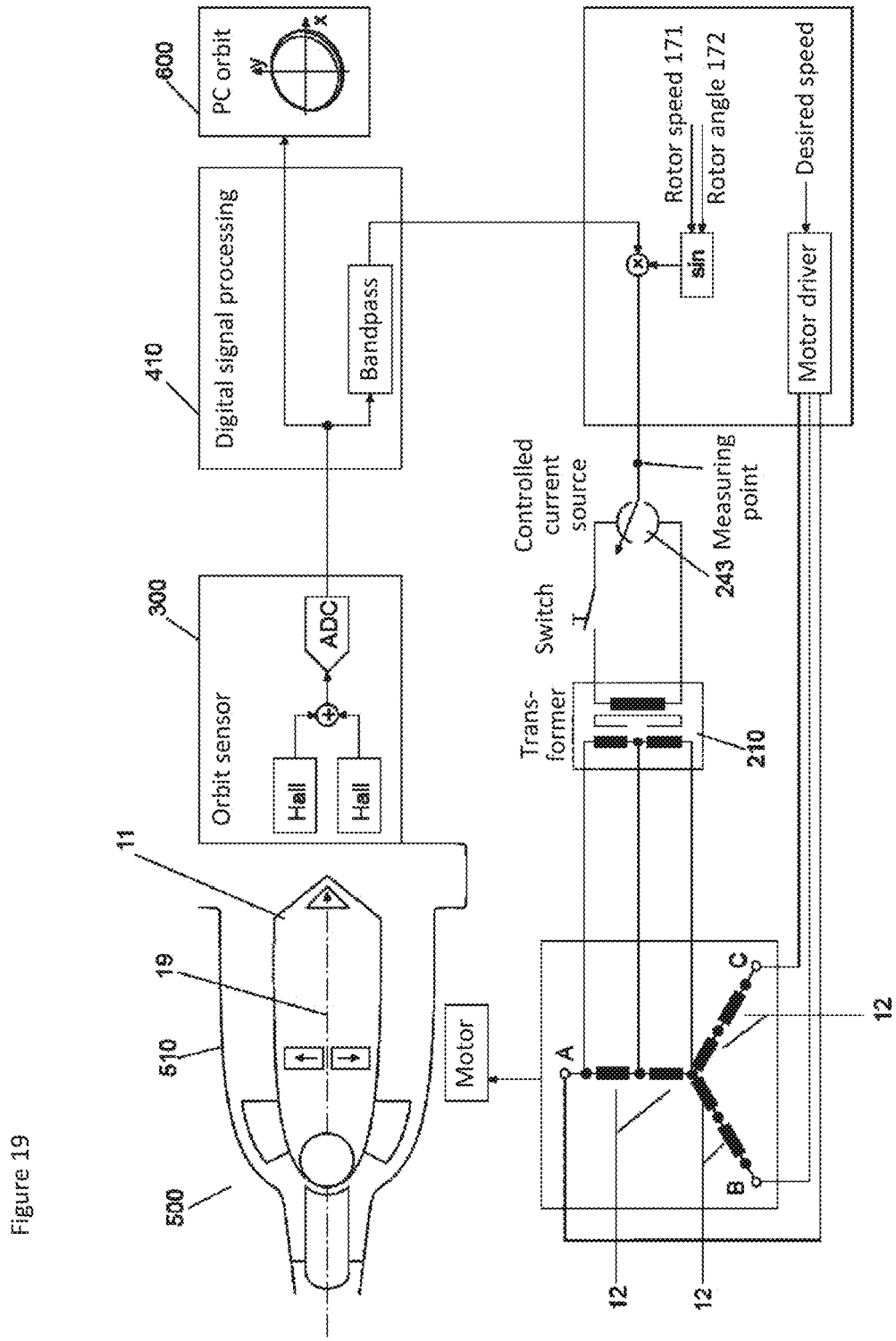
FIG. 19 illustrates an exemplary implementation of the control circuit from FIG. 17 for a pump with a synchronous motor, measurement of the rotor position by means of Hall sensors and coupling of the actuator signal via a transformer.
Figure 20:
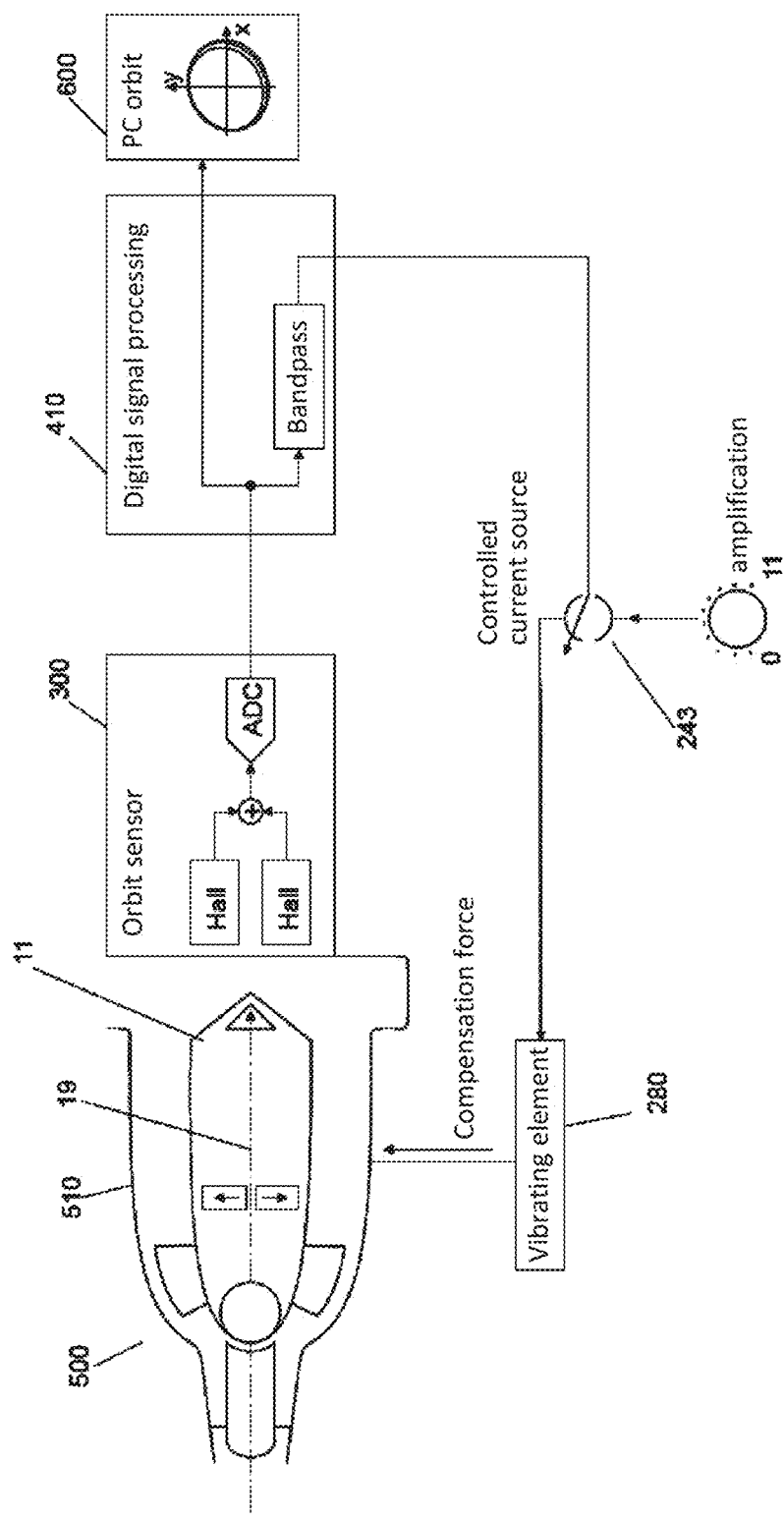
FIG. 20 illustrates an interference compensation by means of a vibrating element as an actuator.
Figure 21:
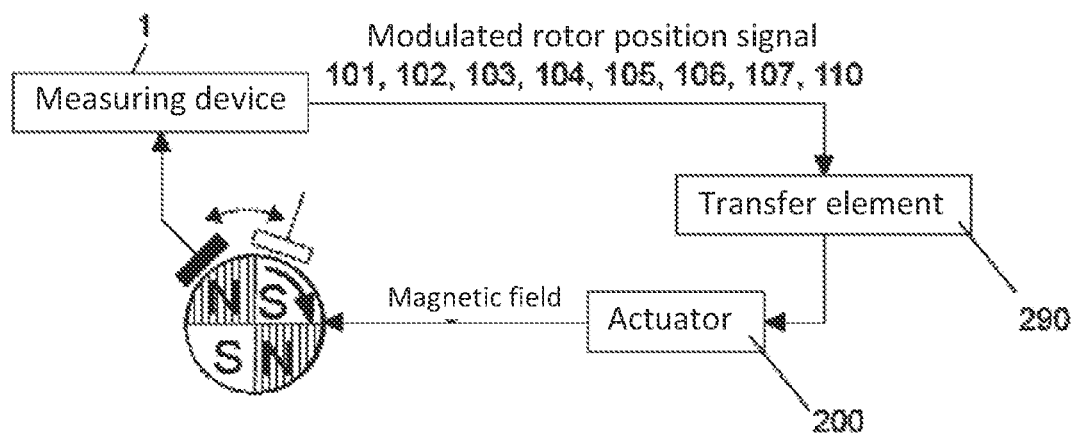
FIG. 21 illustrates a damping control loop with self-mixing.

Using an example of a motor, FIG. 15 shows how the rotor position signal 150 can be used to control an actuator. What is interesting about this example is that the motor coils, which are required anyway for generating a drive magnetic field, can be used as magnetic field sensors 12 and also as actuators. FIG. 15 shows that, for example, the rotor position is detected in phase branch C 1103 using the electrical voltages measured across coils C1 and C2. A regulator 400, for example, a PID regulator, which can optionally be supplemented by further transmission elements, calculates control signals which are used to hold the rotor in a specific position or to dampen the vibration behavior of the rotor. The control signals are transformed using the amplitude modulator 260 such that they have a phase position relative to the rotor rotation angle 172 that results in a stable control loop. The modulated signal is impressed with the aid of a controlled current source 243 into the primary winding 242 of a transformer which, together with the secondary windings 240 and 241, forms the actuator coupling unit 210.

A current 230 is impressed into the coil A1 and a current 231 into the coil A2 via the secondary windings 240 and 241, with the currents in this example oriented such that they cancel out their effect on the phase connection A 2101 and thus also exert no Influence on voltages and currents at the other phase connections 2102 and 2103. This symmetrical way of impressing the current into phase A 1101 can alternatively be replaced by an asymmetrical way of impressing the current, for example, by allowing the actuator coupling unit 210 to be coupled into only one coil 12 A1 or A2.

To clarify the use of and to hereby provide notice to the public, the phrases "at least one of <A>, <B>, . . . and <N>" or "at least one of <A>, <B>, . . . or <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

The present disclosure includes, among other things, the following aspects:

1. A rotary machine comprising
   a stator (13) and a rotatably mounted rotor (11), which is designed to move relative to the stator (13), one or more magnetic field sensors (12) arranged stationary relative to the stator (13) at a radial distance from an axis (20) which is stationary relative to the stator (13), at least one measuring device (1), which is designed to detect magnetic field changes with the aid of the aforementioned magnetic field sensors (12),
   a rotor (11), which is designed to generate one or more electrical signals (101, 102, 103, 104, 105, 106, 107, 110) in each case with one or more constant magnetic source voltages and with one or more of the magnetic field sensors (12), said signals having signal components which correspond to the rotor rotation frequency (171) and to the distance between the magnetic field sensor (12) and the rotor (11) in each case,
   characterized by
   a demodulator unit (4) which is designed to carry out a demodulation of signals (101, 102, 103, 104, 105, 106, 107, 110, 120, 130) generated by or derived from the magnetic field sensors (12), said signals having signal components which correspond to the rotor rotational frequency (171) and to the respective distance between the magnetic field sensor (12) and rotor (11), so that a signal (140) is generated which corresponds to the distance between the rotor (11) and the magnetic field sensor (12) assigned to the specific signal.
2. The rotary machine according to aspect 1, characterized in that the rotary machine is a motor.
3. The rotary machine according to any one of the preceding aspects, characterized in that the magnetic field sensors (12)
   are designed as coils and/or
   are designed as motor coils and are designed to detect magnetic field changes and to generate a magnetic field suitable for driving the rotor.
4. The rotary machine according to any one of the preceding aspects, characterized by
   a device (7), which is designed to provide the rotor rotation frequency (171),
   a demodulator unit (4), which is designed to use the rotor rotation frequency (171) in the demodulation.
5. The rotary machine according to any one of the preceding aspects, characterized by a first processing unit (2), which is designed to superimpose and/or filter one or more electrical signals (101, 102, 103, 104, 105, 106, 107, 110) of the aforementioned magnetic field sensors (12) into one or more signals (120), such that the signal component in the respectively resulting signal, which contains information about the distance (141) between the rotor (11) and the respective magnetic field sensor (12), is in each case amplified in relation to other signal components.
6. The rotary machine according to any one of the preceding aspects, characterized by
   a second processing unit (5), which is connected downstream of the demodulator (4) and which is designed to generate one or more rotor position signals (150) from the demodulated signals (140) and preferably a control unit (6), which is designed to generate control signals (160) from the rotor position signals (150).
7. The rotary machine according to any one of the preceding aspects, characterized by a data collection unit (8), which is designed to store one or more determined position values of the rotor (150).
8. A method using an arrangement according to any one of the preceding aspects, characterized in that
   one or more electrical signals (101, 102, 103, 104, 105, 106, 107, 110) are measured at the magnetic field sensors (12)
   and one or more signals (101, 102, 103, 104, 105, 106, 107, 110, 120, 130) measured at the magnetic field sensors (12) or derived therefrom are demodulated.
9. The method according to aspect 8, characterized in that the rotor rotation frequency (171) is used for demodulation and preferably the rotor rotation angle (172) for demodulation.
10. The method according to any one of aspects 8 to 9, characterized in that one or more electrical signals (101, 102, 103, 104, 105, 106, 107, 110) of the aforementioned magnetic field sensors (12) are processed into one or more signals (120) such that the signal component in the respectively resulting signal, which contains information about the distance (141) between the rotor (11) and the respective magnetic field sensor (12), is in each case amplified relative to other signal components.
11. The method according to any one of aspects 8 to 10, characterized in that at least one or more components of a rotor position (150) and/or a linear displacement speed and/or a linear acceleration of the rotor axis (19') is determined from the demodulated signals (140).
12. The method according to aspect 11, characterized in that control signals (160) are generated from the rotor position signals (150).
13. The method according to any one of aspects 11 to 12, characterized in that a force and/or a torque acting on the rotor is determined from the rotor position signals (150).
14. The method according to any one of aspects 11 to 13, characterized in that one or more determined rotor position values (150) are stored in a data collection unit (8).
15. A blood pump system comprising a rotary machine according to any one of aspects 1 to 7.

Some features of the invention, which are shown in particular in FIGS. 16 to 23, are also reflected in the following aspects:

1. A rotary machine comprising
   a stator (13) and
   a rotatably mounted rotor (11), which is designed to move relative to the stator (13), with one or more coils (12) arranged stationary relative to the stator (13) at a radial distance from an axis (20) that is stationary relative to the stator (13) and
   at least one rotor position detector (300), which is designed to provide one or more signals (101, 102, 103, 104, 105, 106, 107, 110, 150) which represent a spatial position of the rotor (11) relative to one or more spatial reference points (10) of the stator (13),
   characterized by
   at least one actuator coupling unit (210), which is designed to impress an electric coil current (162) into at least one of the coils (12), with the electric coil current (162) impressed in each case containing at least one amplitude-modulated signal component (161), the carrier oscillation frequency (176) of which corresponds to the product of the number of pole pairs of the rotor (11) and rotor rotation frequency (171) and the modulation signal (179) of which is formed by one or more rotor position signals (150) and/or control signals (160), which are designed to influence the spatial position of the rotor (11) and the coils (12), which are designed to generate one or more magnetic fields acting on the rotor (11), said magnetic fields corresponding to the electric coil current (162) impressed in each case, and the rotor (11), which is designed, with one or more stationary magnetic fields relative to the rotor (11), each magnetic field of which having a constant magnetic source voltage, to demodulate the magnetic fields corresponding to the impressed electrical coil currents (162) into one or more translational forces acting on the rotor (11).

2. The rotary machine according to aspect 1, characterized in that the rotary machine is a motor.
3. The rotary machine according to aspect 1, characterized in that it is a driven rotary machine.
4. The rotary machine according to any one of aspects 1 or 2, characterized in that the coils (12) are designed as motor coils.
5. The rotary machine according to aspect 4, characterized in that one or more of the actuator coupling units (210) are designed to impress the electrical coil currents (162) into at least one motor coil (12) such that a current equality in the motor coils (12) belonging to the respective motor phase (1101, 1102, 1103) is canceled and as a result at least one force is exerted on the rotor (11).
6. The rotary machine according to aspect 4 or 5, characterized in that one or more of the actuator coupling units (210) are designed to impress the electrical coil currents (162) in at least two coils (12) of a phase such that the impressed electrical coil currents (162) cancel each other out at the associated phase connection (2101, 2102, 2103) and at the neutral point (2104).
7. The rotary machine according to any one of the preceding aspects, characterized in that one or more of the spatial reference points (10) used for detecting the rotor position (300) are arranged in a spatially different position than one or more of the coils (12).
8. The rotary machine according to any one of aspects 4 to 6, characterized in that the rotor position detection (300) is based on one or more of the signals (101, 102, 103, 104, 105, 106, 107, 110) at the motor coils (12) of a first motor phase (1101, 1102, 1103) and the actuator coupling unit (210) acts on the motor coils (12) of a second motor phase (1101, 1102, 1103).
9. The rotary machine according to any one of aspects 1 to 8, characterized by an actuator coupling unit (210), which is designed to couple the electric coil currents (162) in one or more coils (12) inductively with coils (240, 241, 242).
10. The rotary machine according to any one of aspects 1 to 8, characterized by an actuator coupling unit (210), which is designed to couple the electrical coil currents (162) into one or more coils (12) using a regulated bypass (245, 246).
11. The rotary machine according to any one of aspects 1 to 8, characterized by an actuator coupling unit (210), which is designed to couple the electrical coil currents (162) into one or more coils (12) using one or more regulated current sources (247, 248).
12. The rotary machine according to any one of the preceding aspects, characterized by a control device (6), which is designed to generate one or more of the control signals (160) from one or more of the signals (101, 102, 103, 104, 105, 106, 107, 110, 150) representing the spatial position of the rotor (11) relative to one or more of the spatial reference points (10) of the stator (13), a modulator unit (260), which is designed to generate one or more of the amplitude-modulated signal components (161).

13. The rotary machine according to any one of aspects 1 to 11, characterized by a transmission element (290), which is designed to modify and/or superimpose one or more of the electrical signals (101, 102, 103, 104, 105, 106, 107, 110) that can be measured on the coils (12) using a linear transfer function into the amplitude-modulated signal components (161).
14. The rotary machine according to any one of the preceding aspects, characterized by a data collection unit (8), which is designed to store one or more of the signals (101, 102, 103, 104, 105, 106, 107, 110, 150) representing the spatial position of the rotor (11) relative to one or more of the spatial reference points (10) of the stator (13) and/or the associated control signals (160).
15. A method using an arrangement according to any one of the preceding aspects, characterized in that rotor resonances are damped.
16. A blood pump system comprising a rotary machine according to any one of aspects 1 to 15.

The invention claimed is:

1. A rotary machine comprising
a stator and a rotatably mounted rotor configured to move relative to the stator, one or more magnetic field sensors arranged stationary relative to the stator at a radial distance from an axis which is stationary relative to the stator, at least one measuring device, which configured to detect magnetic field changes with the aid of the aforementioned magnetic field sensors;
a rotor configured to generate one or more electrical signals in each case with one or more constant magnetic source voltages and with one or more of the magnetic field sensors, said electrical signals having signal components which correspond to the rotor rotation frequency and to the distance between the magnetic field sensor and the rotor in each case; and
a demodulator unit configured to carry out a demodulation of signals generated by or derived from the magnetic field sensors, said signals having signal components which correspond to the rotor rotational frequency and to a respective distance between the magnetic field sensor and rotor, such that a signal is generated which corresponds to the distance between the rotor and the magnetic field sensor assigned to the specific signal.

2. The rotary machine of claim 1, wherein at least one magnetic field sensor configured as a motor coil and configured to detect magnetic field changes and to generate a magnetic field suitable for driving the rotor.

3. The rotary machine of claim 1, wherein at least one magnetic field sensor is configured as a coil.

4. The rotary machine of claim 1, wherein the rotary machine is a motor.

5. The rotary machine of claim 1, wherein
a device configured to provide the rotor rotation frequency,
demodulator unit configured to use the rotor rotation frequency in the demodulation.

6. The rotary machine of claim 1, wherein a first processing unit configured to superimpose and/or filter one or more electrical signals of the aforementioned magnetic field sensors into one or more signals, such that the signal component in the respectively resulting signal, which contains information about the distance between the rotor and the respective magnetic field sensor, is in each case amplified in relation to other signal components.

7. The rotary machine of claim 1, wherein
a second processing unit, which is connected downstream of the demodulator and which is configured to generate one or more rotor position signals from the demodulated signals and
a control unit configured to generate control signals from the rotor position signals.

8. The rotary machine of claim 1, wherein a data collection unit configured to store one or more determined position values of the rotor.

9. A method using the rotary machine of claim 1, wherein one or more electrical signals are measured at the magnetic field sensors and one or more signals measured at the magnetic field sensors or derived therefrom are demodulated.

10. The rotary machine of claim 1, wherein the rotary machine is included in a blood pump system.

11. The method of claim 9, wherein the rotor rotation frequency for demodulation and the rotor rotation angle is used for demodulation.

12. The method of claim 9, wherein one or more electrical signals of the aforementioned magnetic field sensors are processed into one or more signals such that the signal component in the respectively resulting signal, which contains information about the distance between the rotor and the respective magnetic field sensor, is in each case amplified relative to other signal components.

13. The method of claim 9, wherein at least one or more components of a rotor position and/or a linear displacement speed and/or a linear acceleration of the rotor axis is determined from the demodulated signals.

14. The method of claim 13, wherein control signals are generated from the rotor position signals.

15. The method of claim 13, wherein a force and/or a torque acting on the rotor is determined from the rotor position signals.

16. The method of claim 13, wherein one or more determined rotor position values are stored in a data collection unit.

* * * * *